US008343195B2

(12) United States Patent
Rathbun et al.

(10) Patent No.: US 8,343,195 B2
(45) Date of Patent: Jan. 1, 2013

(54) DRILL-TAP-SCREW DRILL GUIDE

(75) Inventors: David S. Rathbun, Gap, PA (US); Sean S. Suh, Kirkland, WA (US); Christoph Andreas Roth, West Chester, PA (US); Lan Anh Nguyen Duong, Denver, PA (US); Christopher J. Ryan, West Chester, PA (US)

(73) Assignee: Synthes USA, LLC, West Chester, PA (US)

( * ) Notice: Subject to any disclaimer, the term of this patent is extended or adjusted under 35 U.S.C. 154(b) by 217 days.

(21) Appl. No.: 12/823,755

(22) Filed: Jun. 25, 2010

(65) Prior Publication Data

US 2010/0324566 A1 Dec. 23, 2010

Related U.S. Application Data

(60) Division of application No. 11/255,221, filed on Oct. 19, 2005, now Pat. No. 7,763,029, which is a continuation-in-part of application No. 10/823,215, filed on Apr. 12, 2004, now Pat. No. 7,488,327.

(51) Int. Cl.
*A61B 17/90* (2006.01)

(52) U.S. Cl. ........................................ 606/281; 606/104

(58) Field of Classification Search .................... 606/70, 606/71, 280, 281, 286, 289, 290, 294, 96, 606/99, 104, 86 B, 279, 301
See application file for complete search history.

(56) References Cited

U.S. PATENT DOCUMENTS

| | | | |
|---|---|---|---|
| 125,642 A | 4/1872 | Whitus |
| 232,851 A | 10/1880 | Rutter |
| 413,178 A | 10/1889 | Doe |
| 568,932 A | 10/1896 | Wilcox |
| 569,896 A | 10/1896 | Cauwenberg |
| 631,572 A | 8/1899 | Judson |
| 679,693 A | 7/1901 | Burkhart |
| 696,902 A | 4/1902 | Gray, Sr. |
| 854,956 A | 5/1907 | Martin |
| 1,177,344 A | 3/1916 | Linderman |
| 1,308,798 A | 7/1919 | Masland |
| 1,414,060 A | 4/1922 | Willson et al. |
| 1,430,951 A | 10/1922 | Crammer |
| 1,479,325 A | 1/1924 | Schubnel |
| 1,598,726 A | 9/1926 | Jaynes |
| 1,831,813 A | 11/1931 | Levedahl |
| 2,192,528 A | 3/1940 | Schmidt |
| 2,231,864 A | 2/1941 | Abel |
| 2,294,303 A | 8/1942 | Jagow |
| 2,308,055 A | 1/1943 | Cogsdill |
| 2,338,765 A | 1/1944 | Hartman |
| 2,344,143 A | 3/1944 | Harding |
| 2,402,353 A | 6/1946 | Trautmann |

(Continued)

FOREIGN PATENT DOCUMENTS

CH 655646 A5 5/1996

(Continued)

*Primary Examiner* — Alvin Stewart
*Assistant Examiner* — David Comstock
(74) *Attorney, Agent, or Firm* — Meunier Carlin & Curfman, LLC

(57) ABSTRACT

A surgical drill guide for use with a bone plate having fastener holes oriented at predetermined angles with respect to the plate, the surgical drill guide having at least one alignment drill guiding barrel that is aligned with the respective fastener holes in the bone plate for drilling the holes at the desired range of angles permitted by the plate hole.

7 Claims, 29 Drawing Sheets

U.S. PATENT DOCUMENTS

| | | |
|---|---|---|
| 2,409,525 A | 10/1946 | Andreasson |
| 2,414,292 A | 1/1947 | Ewert |
| 2,494,229 A | 1/1950 | Collison |
| 2,525,669 A | 10/1950 | Hainault |
| 2,526,662 A | 10/1950 | Hipps et al. |
| 2,608,114 A | 8/1952 | Martin et al. |
| 2,710,549 A | 6/1955 | Cogsdill |
| 2,792,726 A | 5/1957 | Vick |
| 2,794,470 A | 6/1957 | Wright |
| 2,833,168 A | 5/1958 | Nelson |
| 3,065,655 A | 11/1962 | Elias |
| 3,083,593 A | 4/1963 | Cotter |
| RE25,860 E | 9/1965 | Elias |
| 3,216,288 A | 11/1965 | Gardner |
| 3,320,832 A | 5/1967 | Jensen |
| 3,336,611 A | 8/1967 | Schepp |
| 3,540,322 A | 11/1970 | Swanson |
| 3,620,637 A | 11/1971 | George |
| 3,682,177 A | 8/1972 | Ames et al. |
| 3,835,849 A | 9/1974 | McGuire |
| 3,867,932 A | 2/1975 | Huene |
| 4,005,527 A | 2/1977 | Wilson et al. |
| 4,019,827 A | 4/1977 | Christianson et al. |
| 4,039,266 A | 8/1977 | O'Connell |
| 4,059,115 A | 11/1977 | Jumashev et al. |
| 4,115,017 A | 9/1978 | Wilhelmsson |
| 4,138,200 A | 2/1979 | Nazarenus |
| 4,142,517 A | 3/1979 | Contreras et al. |
| 4,273,117 A | 6/1981 | Neuhauser |
| 4,319,577 A | 3/1982 | Bofinger et al. |
| 4,341,206 A | 7/1982 | Perrett et al. |
| 4,362,161 A | 12/1982 | Reimels et al. |
| 4,388,921 A | 6/1983 | Sutter et al. |
| 4,450,834 A | 5/1984 | Fischer |
| 4,456,010 A | 6/1984 | Reimels et al. |
| 4,491,132 A | 1/1985 | Aikins |
| 4,521,145 A | 6/1985 | Bieler |
| 4,528,980 A | 7/1985 | Kenna |
| 4,549,538 A | 10/1985 | Schadrack, III et al. |
| 4,600,006 A | 7/1986 | Baker |
| 4,605,345 A | 8/1986 | Giughese |
| 4,649,919 A | 3/1987 | Thimsen et al. |
| 4,699,550 A | 10/1987 | Baker |
| 4,705,436 A | 11/1987 | Robertson |
| 4,710,075 A | 12/1987 | Davison |
| 4,730,613 A | 3/1988 | Gordy |
| 4,750,489 A | 6/1988 | Berkman et al. |
| 4,821,716 A | 4/1989 | Ghajar et al. |
| 4,830,001 A | 5/1989 | Walus |
| 4,877,359 A | 10/1989 | Kolacek |
| 4,884,571 A | 12/1989 | Baker |
| 4,904,130 A | 2/1990 | Gorman |
| 4,969,781 A | 11/1990 | Fahrner et al. |
| 5,026,376 A | 6/1991 | Greenberg |
| 5,066,288 A | 11/1991 | Deniega et al. |
| 5,071,293 A | 12/1991 | Wells |
| 5,078,552 A | 1/1992 | Albel |
| 5,122,146 A | 6/1992 | Chapman et al. |
| 5,129,907 A | 7/1992 | Heldreth et al. |
| 5,133,720 A | 7/1992 | Greenberg |
| 5,147,164 A | 9/1992 | Fraver |
| 5,147,367 A | 9/1992 | Ellis |
| 5,171,244 A | 12/1992 | Caspari et al. |
| 5,180,384 A | 1/1993 | Mikhail |
| 5,180,388 A | 1/1993 | DiCarlo |
| 5,190,422 A | 3/1993 | Lechot |
| 5,190,548 A | 3/1993 | Davis |
| 5,207,681 A | 5/1993 | Ghadjar et al. |
| 5,207,753 A | 5/1993 | Badrinath |
| 5,222,848 A | 6/1993 | Kuang-Wu |
| 5,228,459 A | 7/1993 | Caspari et al. |
| 5,228,811 A | 7/1993 | Potter |
| 5,350,380 A | 9/1994 | Goble et al. |
| 5,354,300 A | 10/1994 | Goble et al. |
| 5,364,399 A | 11/1994 | Lowery et al. |
| 5,374,269 A | 12/1994 | Rosenberg |
| 5,374,270 A | 12/1994 | McGuire et al. |
| 5,382,120 A | 1/1995 | Parsons |
| 5,382,250 A | 1/1995 | Kraus |
| 5,383,859 A | 1/1995 | Sewell, Jr. |
| 5,387,218 A | 2/1995 | Meswania |
| 5,409,490 A | 4/1995 | Ethridge |
| 5,409,493 A | 4/1995 | Greenberg |
| 5,423,823 A | 6/1995 | Schmieding |
| 5,423,824 A | 6/1995 | Akerfeldt et al. |
| 5,437,675 A | 8/1995 | Wilson |
| 5,437,677 A | 8/1995 | Shearer et al. |
| 5,447,512 A | 9/1995 | Wilson et al. |
| 5,465,492 A | 11/1995 | Bond |
| 5,486,177 A | 1/1996 | Mumme et al. |
| 5,509,762 A | 4/1996 | Fredricksen |
| 5,520,692 A | 5/1996 | Ferrante |
| 5,527,316 A | 6/1996 | Stone et al. |
| 5,536,271 A | 7/1996 | Daly et al. |
| 5,549,613 A | 8/1996 | Goble et al. |
| 5,562,673 A | 10/1996 | Koblish et al. |
| 5,573,537 A | 11/1996 | Rogozinski |
| 5,575,794 A | 11/1996 | Walus et al. |
| 5,578,037 A | 11/1996 | Sanders et al. |
| 5,607,431 A | 3/1997 | Dudasik et al. |
| 5,624,214 A | 4/1997 | Carroll |
| 5,630,683 A | 5/1997 | Smith |
| 5,649,791 A | 7/1997 | Connolly |
| 5,653,712 A | 8/1997 | Stern |
| 5,658,291 A | 8/1997 | Techiera |
| 5,667,509 A | 9/1997 | Westin |
| 5,669,915 A | 9/1997 | Caspar et al. |
| 5,681,333 A | 10/1997 | Burkhart et al. |
| 5,700,291 A | 12/1997 | Kuslich et al. |
| 5,713,905 A | 2/1998 | Goble et al. |
| 5,735,855 A | 4/1998 | Bradley |
| 5,741,267 A | 4/1998 | Jorneus et al. |
| 5,743,916 A | 4/1998 | Greenberg et al. |
| 5,746,551 A | 5/1998 | Skaggs |
| 5,746,552 A | 5/1998 | Tsui et al. |
| 5,746,743 A | 5/1998 | Greenberg |
| 5,762,639 A | 6/1998 | Gibbs |
| 5,785,522 A | 7/1998 | Bergstrom et al. |
| 5,785,714 A | 7/1998 | Morgan et al. |
| 5,797,917 A | 8/1998 | Boyd et al. |
| 5,810,828 A | 9/1998 | Lightman et al. |
| 5,827,290 A | 10/1998 | Bradley |
| 5,836,950 A | 11/1998 | Hansson |
| 5,851,207 A | 12/1998 | Cesarone |
| D404,126 S | 1/1999 | Asfora |
| 5,855,581 A | 1/1999 | Koblish et al. |
| 5,857,995 A | 1/1999 | Thomas et al. |
| 5,865,834 A | 2/1999 | McGuire |
| 5,876,405 A | 3/1999 | Del Rio et al. |
| 5,879,353 A | 3/1999 | Terry |
| 5,885,293 A | 3/1999 | McDevitt |
| 5,888,034 A | 3/1999 | Greenberg |
| 5,890,897 A | 4/1999 | Kruger et al. |
| 5,893,684 A | 4/1999 | Skaggs |
| 5,895,389 A | 4/1999 | Schenk et al. |
| 5,897,560 A | 4/1999 | Johnson |
| 5,899,908 A | 5/1999 | Kuslich et al. |
| 5,908,272 A | 6/1999 | Hoag et al. |
| 5,908,423 A | 6/1999 | Kashuba et al. |
| 5,915,893 A | 6/1999 | Miyanaga |
| 5,919,196 A | 7/1999 | Bobic et al. |
| 5,928,240 A | 7/1999 | Johnson |
| 5,931,838 A | 8/1999 | Vito |
| 5,931,841 A | 8/1999 | Ralph |
| 5,941,706 A | 8/1999 | Ura |
| 5,947,654 A | 9/1999 | Blankenship et al. |
| 5,947,971 A | 9/1999 | Kuslich et al. |
| 5,954,722 A | 9/1999 | Bono |
| 5,976,143 A | 11/1999 | McCue |
| 5,976,145 A | 11/1999 | Kennefick |
| 5,989,260 A | 11/1999 | Yao |
| 5,993,453 A | 11/1999 | Bullara et al. |
| 6,013,083 A | 1/2000 | Bennett |
| 6,015,411 A | 1/2000 | Ohkoshi et al. |
| 6,022,354 A | 2/2000 | Mercuri et al. |
| 6,033,409 A | 3/2000 | Allotta |
| 6,059,790 A | 5/2000 | Sand et al. |

| | | |
|---|---|---|
| 6,063,088 A | 5/2000 | Winslow |
| 6,071,284 A | 6/2000 | Fox |
| 6,096,042 A | 8/2000 | Herbert |
| 6,110,175 A | 8/2000 | Scholl |
| 6,110,178 A | 8/2000 | Zech et al. |
| 6,139,550 A | 10/2000 | Michelson |
| 6,146,385 A | 11/2000 | Torrie et al. |
| 6,159,214 A | 12/2000 | Michelson |
| 6,162,226 A | 12/2000 | DeCarlo, Jr. et al. |
| 6,171,312 B1 | 1/2001 | Beaty |
| 6,183,478 B1 | 2/2001 | Konieczynski |
| 6,193,721 B1 | 2/2001 | Michelson |
| 6,193,722 B1 | 2/2001 | Zech et al. |
| 6,203,253 B1 | 3/2001 | Perrault |
| 6,206,885 B1 | 3/2001 | Ghahremani et al. |
| 6,209,886 B1 | 4/2001 | Estes et al. |
| 6,235,034 B1 | 5/2001 | Bray |
| 6,235,035 B1 | 5/2001 | Boukhris |
| 6,241,434 B1 | 6/2001 | Ajimi |
| 6,277,121 B1 | 8/2001 | Burkinshaw et al. |
| 6,287,313 B1 | 9/2001 | Sasso |
| 6,306,139 B1 | 10/2001 | Fuentes |
| 6,306,142 B1 | 10/2001 | Johanson et al. |
| 6,325,806 B1 | 12/2001 | Fox |
| 6,342,057 B1 | 1/2002 | Brace et al. |
| 6,358,253 B1 | 3/2002 | Torrie et al. |
| 6,361,537 B1 | 3/2002 | Anderson |
| 6,379,364 B1 | 4/2002 | Brace et al. |
| 6,383,186 B1 | 5/2002 | Michelson |
| 6,398,783 B1 | 6/2002 | Michelson |
| 6,402,757 B1 | 6/2002 | Moore, III et al. |
| 6,416,528 B1 | 7/2002 | Michelson |
| 6,428,542 B1 | 8/2002 | Michelson |
| 6,436,103 B1 | 8/2002 | Suddaby |
| 6,440,139 B2 | 8/2002 | Michelson |
| 6,454,771 B1 | 9/2002 | Michelson |
| 6,471,711 B2 | 10/2002 | Irie et al. |
| 6,499,221 B1 | 12/2002 | Kuhn et al. |
| 6,514,258 B1 | 2/2003 | Brown et al. |
| 6,517,581 B2 | 2/2003 | Blamey |
| 6,524,312 B2 | 2/2003 | Landry et al. |
| 6,527,776 B1 | 3/2003 | Michelson |
| 6,543,971 B2 | 4/2003 | Mawhinney |
| 6,547,562 B2 | 4/2003 | Kumar |
| 6,547,795 B2 | 4/2003 | Schneiderman |
| 6,562,046 B2 | 5/2003 | Sasso |
| 6,562,055 B2 | 5/2003 | Walen |
| 6,592,586 B1 | 7/2003 | Michelson |
| 6,592,588 B1 | 7/2003 | Bobic et al. |
| 6,610,065 B1 | 8/2003 | Branch et al. |
| 6,616,666 B1 | 9/2003 | Michelson |
| 2001/0000532 A1 | 4/2001 | Michelson |
| 2002/0022847 A1 | 2/2002 | Ray et al. |
| 2002/0042624 A1 | 4/2002 | Johanson et al. |
| 2002/0045896 A1 | 4/2002 | Michelson |
| 2002/0058958 A1 | 5/2002 | Walen |
| 2002/0082606 A1 | 6/2002 | Suddaby |
| 2002/0091392 A1 | 7/2002 | Michelson |
| 2002/0128655 A1 | 9/2002 | Michelson |
| 2002/0156481 A1 | 10/2002 | Boyd et al. |
| 2002/0193780 A1 | 12/2002 | Karray et al. |
| 2002/0193799 A1 | 12/2002 | Chappuis et al. |
| 2003/0018335 A1 | 1/2003 | Michelson |
| 2003/0018337 A1 | 1/2003 | Davis |
| 2003/0022132 A1 | 1/2003 | Jesch |
| 2003/0040748 A1 | 2/2003 | Aikins et al. |
| 2003/0045880 A1 | 3/2003 | Michelson |
| 2003/0055430 A1 | 3/2003 | Kim |
| 2003/0083667 A1 | 5/2003 | Ralph et al. |
| 2003/0105461 A1 | 6/2003 | Putnam |
| 2003/0135213 A1 | 7/2003 | LeHuec et al. |
| 2003/0153918 A1 | 8/2003 | Putnam et al. |
| 2003/0187442 A1 | 10/2003 | Richelsoph et al. |
| 2003/0225409 A1 | 12/2003 | Freid et al. |

FOREIGN PATENT DOCUMENTS

| | | |
|---|---|---|
| DE | 3214182 A1 | 10/1983 |
| DE | 3800482 A1 | 7/1989 |
| DE | 10047268 C1 | 3/2002 |
| EP | 350291 A2 | 1/1990 |
| EP | 386532 A1 | 9/1990 |
| EP | 421485 A1 | 4/1991 |
| EP | 460447 A1 | 12/1991 |
| EP | 463551 A1 | 1/1992 |
| EP | 490355 A1 | 6/1992 |
| EP | 386532 B1 | 9/1992 |
| EP | 506213 A1 | 9/1992 |
| EP | 589108 A1 | 3/1994 |
| EP | 490355 B1 | 6/1994 |
| EP | 350291 B1 | 9/1994 |
| EP | 460447 B1 | 10/1994 |
| EP | 465551 B1 | 12/1995 |
| EP | 589108 B1 | 7/1996 |
| EP | 823242 A2 | 2/1998 |
| EP | 823242 A3 | 7/1998 |
| EP | 928599 A2 | 7/1999 |
| EP | 928599 A3 | 7/1999 |
| EP | 1226786 A2 | 7/2002 |
| EP | 1285630 A1 | 2/2003 |
| EP | 1226 786 A3 | 7/2003 |
| FR | 2554709 A1 | 5/1985 |
| FR | 2633538 A1 | 1/1990 |
| FR | 2735008 A1 | 12/1996 |
| GB | 2181076 A | 4/1987 |
| GB | 2269333 A | 2/1994 |
| JP | 2236331 A | 9/1990 |
| JP | 4231947 A | 8/1992 |
| JP | 5103790 A | 4/1993 |
| JP | 10113884 A | 5/1998 |
| JP | 10118084 A | 5/1998 |
| JP | 11188043 A | 7/1999 |
| JP | 2002102236 A | 4/2002 |
| WO | WO 9117715 A1 | 11/1991 |
| WO | WO 9324061 A1 | 12/1993 |
| WO | WO 9848707 A1 | 11/1998 |
| WO | WO 9848708 A1 | 11/1998 |
| WO | WO 9952453 A2 | 10/1999 |
| WO | WO 03007826 A1 | 1/2003 |

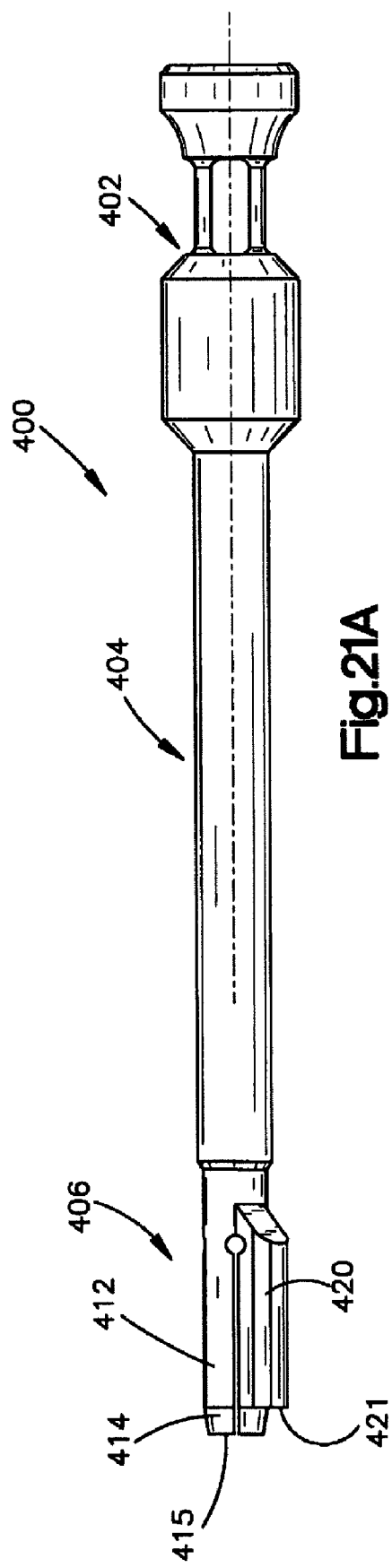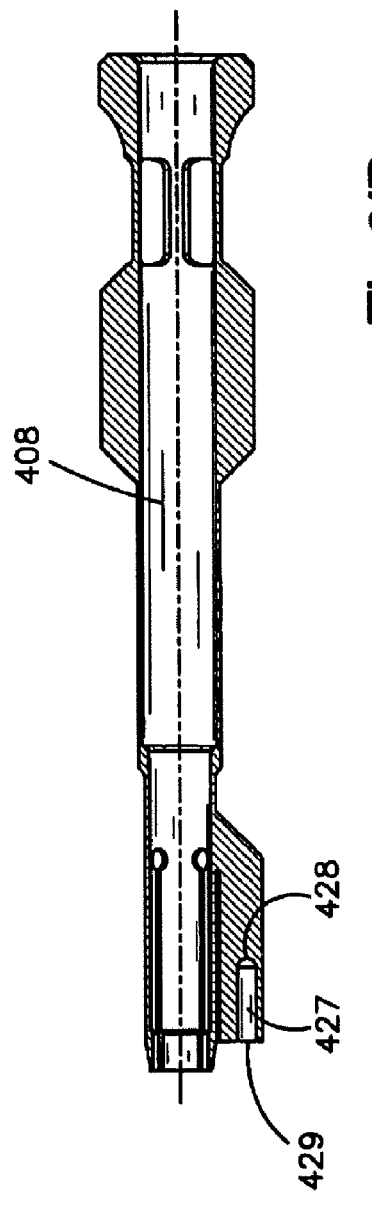
Fig.21A
Fig.21B

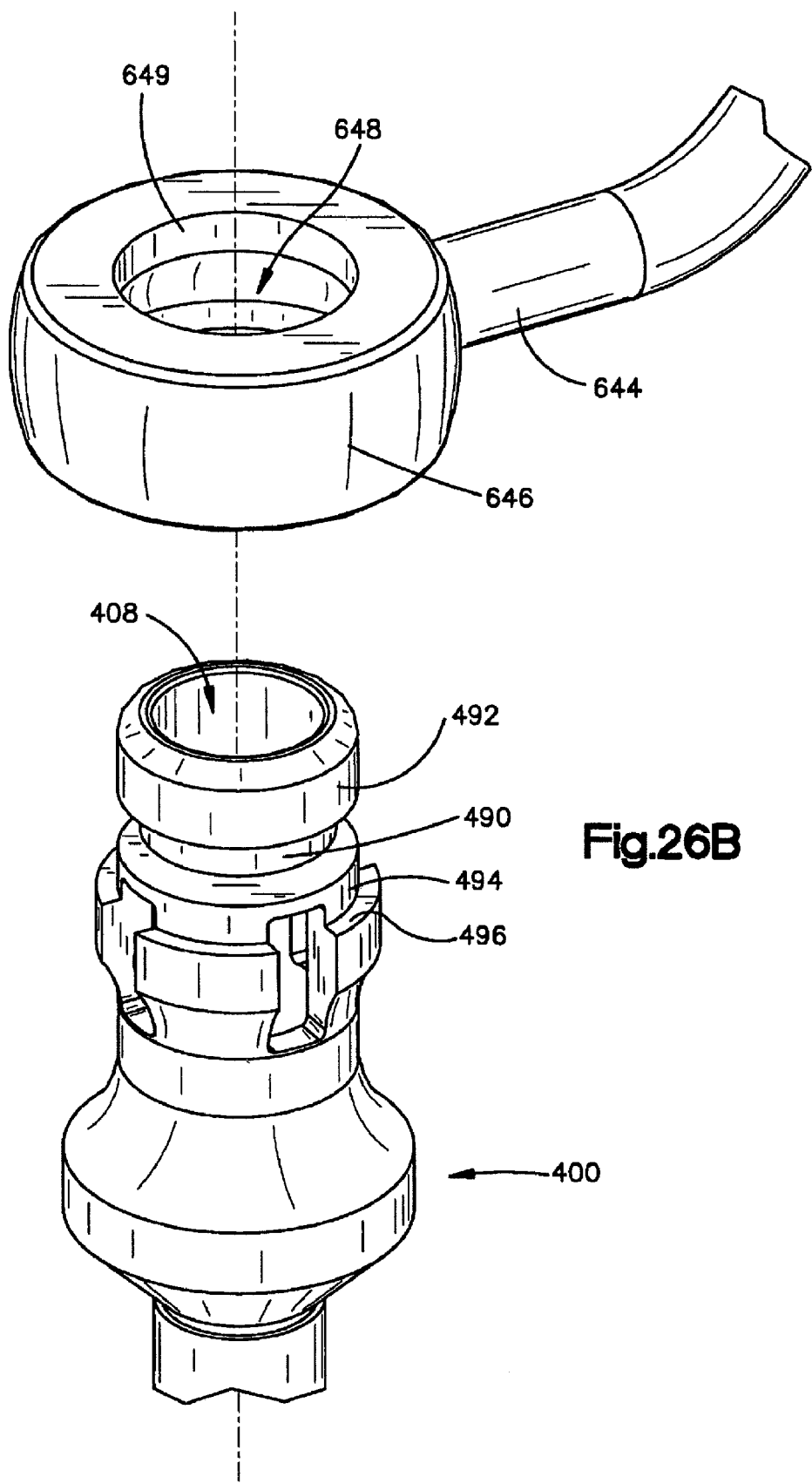

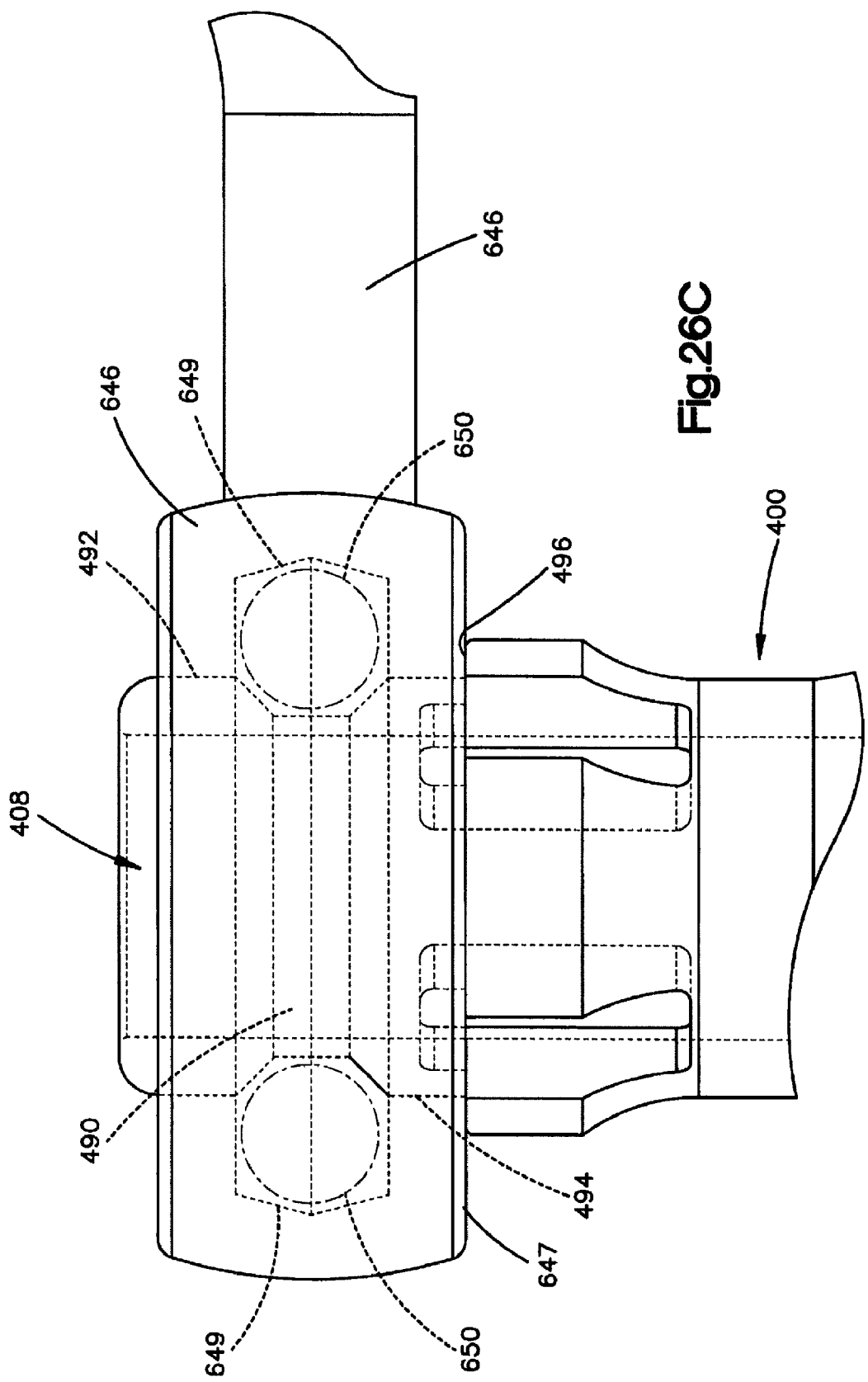

DRILL-TAP-SCREW DRILL GUIDE

CROSS-REFERENCE TO RELATED APPLICATION

This application is a divisional application of U.S. patent application Ser. No. 11/255,221 filed Oct. 19, 2005 now U.S. Pat. No. 7,763,029, which is a continuation-in-part of U.S. patent application Ser. No. 10/823,215, filed Apr. 12, 2004, now U.S. Pat. No. 7,488,327, the contents of which are expressly incorporated by reference herein.

FIELD OF THE INVENTION

The present invention relates to the field of surgical drill guides, and in particular relates to drill guides that may be associated with a bone plate for providing precise alignment of hole forming tools with the bone screw holes of the plate. More particularly, the surgical drill guide assembly provides soft tissue protection and precise alignment of at least one drill tube with bone screw holes of a bone plate, such as for example, a spinal bone plate.

BACKGROUND OF THE INVENTION

The use of surgical fixation plates for a variety of orthopedic applications is widely accepted. The plates are used by surgeons to stabilize, mend, or align a patient's bone as well as alter compression of patient's bones, and are typically fastened to the bones with a plurality of fasteners, such as, screws that are installed through holes in the plate. Proper orientation and alignment of fasteners and secure surgical fixation of the plate can mitigate some of the potential complications after implantation.

Locking bone plates used in spinal applications must be installed with special care, as the plates may be used for long term, intervertebral fixation, bone-fragment fixation, and anterior decompression of vertebra of the spine. The margin for error in spinal surgery is small, particularly because of the sensitivity of the spinal cord and the risk inherent with invasive procedures around the spinal cord. Furthermore, the dimensions of vertebral bone available for setting fasteners are fairly constrained.

Screws, used to secure the plate to the bone, should be properly aligned with the associated fixation plate hole so that each screw is seated correctly within the plate. Any misalignment of the screw within the plate hole risks tissue damage. In addition, improperly seated screws may result in an unstable or insecure connection of the plate to the bony material, thus potentially defeating the usefulness of the plate. Locking plates, in particular, demand precise fastener alignment.

Drill guides are often used to assist the surgeon in aligning the screws with the plate holes. Drill guides for locking plates attach or abut to the plate and generally include a guide tube for guiding hole-forming tools, such as a drill bit.

SUMMARY OF THE INVENTION

A drill guide is provided comprising a guide barrel for receiving a bone tool for creating a hole in bone and an alignment assembly associated with the guide barrel for aligning the bone tool with a selected first or second fastener hole of a bone plate. The alignment assembly may comprise a location post configured to be at least partially received within a recess in the bone plate. Further, the location post may be pivotable about the bone plate recess to allow the guide barrel to be selectively aligned with the first and second fastener holes. The location post alternatively may be configured to axially lock the drill guide to the bone plate.

The location post may further comprise a plurality of resilient finger elements configured to frictionally engage the bone plate recess to thereby axially lock the drill guide to the bone plate. The resilient finger elements also may have at least one ridge configured to engage threads in the bone plate recess.

The alignment assembly further may comprise a housing having a first axial bore configured to slidably receive at least a portion of the location post. The location post and housing further each may have a distal end. The location post may have a retracted position in which the location post distal end is located a first distance from the distal end of the housing. The location post may also have an extended position in which the location post distal end is located a second distance from the distal end of the housing, where the second length is greater than the first length. The alignment assembly further comprising a spring element disposed at least partially within a second axial bore in the housing to bias the location post to the extended position.

The guide barrel further may comprise a bore with a bore axis, and a distal plate-engaging end, wherein the distal plate-engaging end comprises a nose portion configured to be received within the first or second fastener hole to align the bore with the bone screw hole.

The nose portion may comprise a conical shape. Further, the housing first axial bore and the guide barrel bore forming an acute angle therebetween. Thus, when the location post received within the bone plate recess and the location post is in the extended position, the guide barrel distal end may be located a first distance from the top surface of the bone plate. Further, when the location post is received within the bone plate recess and the location post is in the retracted position, the guide barrel distal end may contact the selected bone screw hole. In an alternative embodiment, the location post may be axially fixed to the alignment assembly.

The drill guide may further comprise a handle associated with the guide barrel, and the handle may be configured to be selectively rotatable with respect to the guide barrel in a first plane. The first plane may be substantially perpendicular to the longitudinal axis of the guide barrel bore. A handle swivel assembly may also be provided having a locked position in which the handle can not rotated with respect to the guide barrel, and an unlocked position in which the handle is freely rotatable with respect to the guide barrel. The swivel assembly may comprise at least one non-metallic bearing, and may also comprise a drain hole configured to allow fluid to drain from the assembly subsequent to sterilization of the drill guide.

A surgical drill guide may be provided comprising a handle, a guide barrel having a proximal end associated with the handle and a distal end configured to engage an inner surface of a fastener hole of a bone plate. The guide barrel further may comprise a bore configured to receive a bone cavity forming tool. An alignment assembly may be associated with the guide barrel for aligning the bone tool with a selected first or second fastener hole, the alignment assembly comprising a location post configured to be at least partially received within a recess in the bone plate;

The location post may be pivotable within the recess to allow the guide barrel to be selectively aligned with the first and second fastener holes so that the tool may be extended through the guide barrel to form a cavity in a bone underlying the selected fastener hole. The location post may be configured to axially lock the drill guide to the bone plate. The location post further may comprise a plurality of resilient finger elements configured to frictionally engage the bone plate recess to thereby axially lock the drill guide to the bone plate. The resilient finger elements may further comprise at least one ridge configured to engage threads in the bone plate recess. The alignment assembly may further comprise a housing having a first axial bore configured to slidably receive at least a portion of the location post.

The location post may have a retracted position in which a first length of the location post is received within the bore and an extended position in which a second length of the location post is received within the bore, wherein the first length is greater than the second length.

The alignment assembly further may comprise a spring element disposed at least partially within a second axial bore in the housing to bias the location post to the extended position. The guide barrel further may comprise a bore with a bore axis, and a distal plate-engaging end, wherein the distal plate-engaging end comprises a nose portion configured to be received within the first or second fastener hole to align the bore with the bone screw hole. The nose portion may comprise a conical shape. Further, the housing first axial bore and the guide barrel bore may form an acute angle therebetween.

The location post may be received within the bone plate recess so that when the location post is in the extended position, the guide barrel distal end is located a first distance from the top surface of the bone plate. Further, when the location post is received within the bone plate recess and the location post is in the retracted position, the guide barrel distal end may contact second bone screw hole. Alternatively, the location post may be axially fixed to the alignment assembly.

The drill guide further may comprise a handle associated with the guide barrel, where the handle is configured to be selectively rotatable with respect to the guide barrel in a first plane. The first plane may be substantially perpendicular to the longitudinal axis of the guide barrel bore. The swivel assembly may have a locked position in which the handle can not rotated with respect to the guide barrel, and an unlocked position in which the handle is freely rotatable with respect to the guide barrel. The swivel assembly may further comprise at least one non-metallic bearing. The swivel assembly further may comprise a drain hole configured to allow fluid to drain from the assembly subsequent to sterilization of the drill guide.

A drill guide assembly is provided comprising a guide barrel having a tool receiving portion comprising a longitudinal bore having a bore axis, and an aligning assembly portion. An aligning assembly may be provided comprising a guide barrel engaging portion, a housing and a location post having a post axis. A bone plate may further be provided comprising at least two bone screw holes and a positioning recess, and the positioning recess may be configured to receive at least a portion of the location post, the center of the positioning recess being separated from the center of at least one of the bone screw holes by a first distance. The bore axis may be located a second distance from the location post axis, the first and second distances being substantially equal so that when the location post engages the bone plate recess, the bore is substantially coaxial with the at least one fixation hole.

The drill guide may further comprise a handle member associated with a proximal end of the guide barrel, and the handle member may be pivotable in relation to the guide barrel.

The guide barrel may have at least one depth stop surface configured to coact with a corresponding stop surface of a bone cavity forming tool when the tool is received within the bore to prevent the tool from passing completely through the guide barrel bore. The handle further may have a locked position in which the handle is rotationally coupled to the guide barrel, and an unlocked position in which the handle is freely rotatable with respect to the guide barrel. The handle may further comprise a locking button having an actuation end and a locking end, the locking end having at least one radial projection, the button further having an unactuated position and an actuated position.

The handle may further comprise a bore configured to slidably receive at least a portion of the button, the bore further comprising a radial recess configured to receive the radial projection. A handle extension may be provided having a handle engaging end and a guide barrel engaging end, the handle engaging end having at least one radial groove configured to receive the radial projection; wherein when the handle is in the unactuated position, the radial projection engages the radial recesses of the handle bore and the handle extension to configure the handle in the locked position. Further, when the handle is in the actuated position, the radial projection may engage the radial recess of only one of the handle bore and the handle extension to configure the handle in the unlocked position.

The location post further may comprise a plate engaging end having a plurality of resilient fingers configured to axially lock the drill guide to the bone plate when the location post is engaged with the recess. The location post plate engaging end may have at least one circumferential ridge configured to engage a bottom surface of the bone plate when the location post is engaged with the recess.

A drill guide assembly may further be provided comprising a guide barrel having a tool receiving portion comprising a longitudinal bore having a bore axis, and an aligning assembly portion. An aligning assembly may be provided comprising a guide barrel engaging portion, a housing and a location post having a post axis. A bone plate further may be provided having at least two fastener receiving holes and a drill guide positioning recess, the recess configured to receive at least a portion of the location post, the center of the recess being separated from the center of at least one of the bone screw holes by a first distance. Further, the bore axis may be located a second distance from the location post axis as measured between the distal ends of the guide barrel and the location post, the first and second distances being substantially unequal so that when the location post engages the bone plate recess, the bore is not coaxial with the at least one fixation hole.

The difference between the first and second distances may be from about 0 millimeters (mm) to about 0.8 mm. Alternatively, the second distance may be about .0.5 mm longer than the first distance.

A method for drilling a hole in bone may be provided, comprising the steps of: providing a bone plate having at least a first pair of fastener receiving holes and a drill guide aligning recess; applying the plate to the bone surface; providing a drill guide having a guide bore for receiving a tool and an alignment mechanism associated with the guide bore and including a location post having a proximal alignment mechanism engaging end and a distal plate engaging end; inserting the plate engaging end of the location post into the recess in the bone plate; rotating the location post within the recess in the bone plate to align the guide bore with a first selected one of the pair of fastener receiving holes; inserting and advancing a tool through the guide bore to contact the bone surface underlying the selected fastener receiving hole; and applying rotational and/or axial force to the tool to creating a cavity in the bone underlying the selected fastener receiving hole.

The alignment mechanism may further comprise a spring element to bias the location post distally axially away from the alignment mechanism, the guide bore further comprising a distal end adjacent the distal end of the location post, the guide bore distal end comprising a conical nose portion configured to engage an inner surface of at least one of the pair of fastener receiving holes, wherein the step of aligning the guide bore with a selected one of the pair of fastener receiving holes further comprises engaging the guide bore nose with the inner surface of the at least one of the pair of fastener receiving holes.

The method may further comprise the step of rotating the location post within the hole, slot, or indention in the bone plate to align the guide bore with the second one of the pair of fastener receiving holes; inserting and advancing the tool through the guide bore to contact the bone surface underlying the second fastener receiving hole; and applying rotational and/or axial force to the tool to create a cavity in the bone underlying the second fastener receiving hole. The tool may be an awl, drill or tap.

The method may further comprising the steps of disengaging the location post from the recess in the plate to disassociate the drill guide from the bone plate, inserting a bone fastener through one of the first and second fastener receiving holes and into the cavity in the bone underlying the fastener receiving hole, and engaging the fastener with the fastener receiving hole and the bone to fix the plate to the bone.

The drill guide bore and alignment mechanism may be offset from each other so that when the location post is rotated within the bone plate recess to align the guide bore with a first selected one of the pair of fastener receiving holes, the guide bore axis is offset from the center of the fastener receiving hole.

The method may further comprise the steps of inserting and advancing a tool through the guide bore to contact the bone surface underlying the selected fastener receiving hole; and applying rotational and/or axial force to the tool to creating a cavity in the bone underlying the selected fastener receiving hole comprise creating a cavity having an axis that is not collinear with the axis of the fastener receiving hole.

BRIEF DESCRIPTION OF THE DRAWINGS

Preferred features of the present invention are disclosed in the accompanying drawings, wherein similar reference characters denote similar elements throughout the several views, and wherein:

FIGS. 3A and 3B are a side view and cross sectional detail view, respectively, of the drill guide of FIG. 1, while

FIG. 21A is a side view of an embodiment of the drill guide of FIG. 20A;

FIG. 21B is a cross-sectional view of the drill guide of FIG. 21A;

FIG. 26B in an enlarged view of the embodiment of FIG. 26A, wherein the handle is detached from the drill guide; and FIG. 26C is an enlarged side view of the drill guide and handle of FIG. 26A, wherein the components are transparent for clarity.

DETAILED DESCRIPTION OF THE PREFERRED EMBODIMENTS

Figure 1:
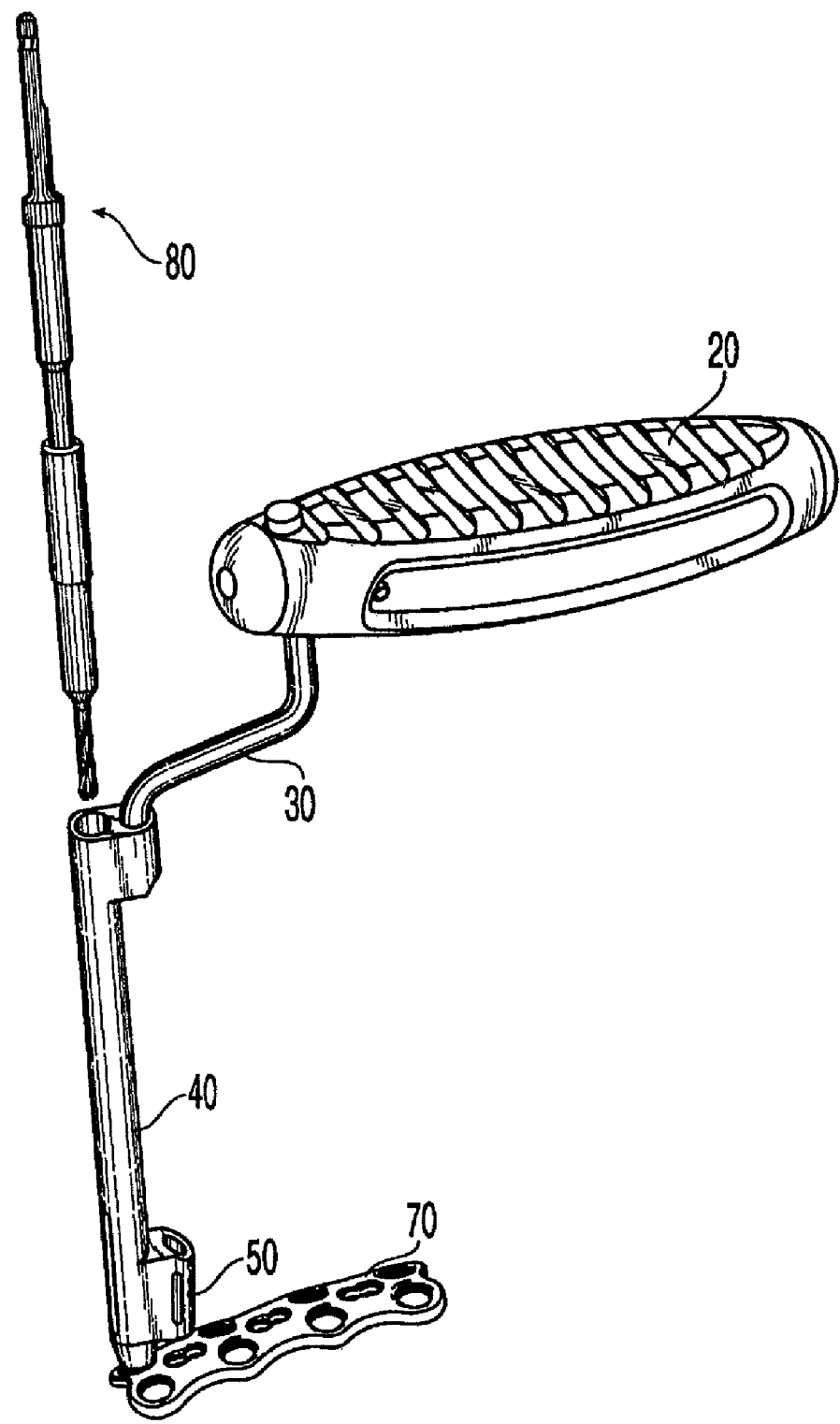
FIG. 1 is a perspective view of a first embodiment of the free hand drill guide assembly, an exemplary bone plate, and an exemplary drill bit.

Referring to FIG. 1, there is shown an exemplary drill guide assembly 10, which is adapted for use with a spinal fixation device, such as for example, a spinal fixation plate 70. An exemplary spinal fixation plate may be that disclosed in co-pending United States non-provisional patent application entitled "Bone Plate with Captive Clips, by Duong, et al., filed Sep. 3, 2003, the entire disclosure of which is expressly incorporated by reference herein. It is noted, however, that while the drill guide assembly is disclosed in conjunction with a spinal fixation plate it is contemplated that the drill guide assembly may be used in conjunction with bone plates used on any portion of the body. Alternatively, in some instances the drill guide may be used without a bone plate. Drill guide assembly 10 generally includes a handle 20, an offset handle extension 30, a guide barrel 40, and a plate aligning mechanism 50. In general, to operate the drill guide assembly 10, a surgeon grasps the handle 20 of the drill guide assembly 10 and aligns the plate aligning mechanism 50 (FIGS. 3A, 3B) with a bone plate 70 such that the location post 52 of the plate aligning mechanism 50 is received within a slot end-hole 72 (FIGS. 2A, 2C) in bone plate 70. When the location post 52 is received within the end hole 72, the drill guide barrel 40 may then be swiveled about the location post 52 to bring the barrel 40 into rough alignment with one of a pair of bone screw holes 74R, L in the bone plate 70. A downward force may then be applied to the handle 20 to force the nose portion 42 of the guide barrel 40 to engage the targeted bone screw hole 74R, L. This engagement serves to precisely align the guide barrel 40 within the bone screw hole 74R, L to assure the hole in the bone will be drilled in the desired location and with the desired trajectory, since the hole will largely control the location of the bone screw placed therein.

With the nose portion 42 of the drill guide barrel 40 engaged with the targeted bone screw hole 74R, L, an awl, drill and tap may be individually and sequentially inserted through the guide barrel 40 to prepare the hole in the bone for receipt of a bone screw. Once preparation of the hole is complete, the guide barrel nose portion 42 may be removed from the bone screw hole 74R, L, and the guide barrel 40 swiveled within the slot end-hole 72 to align with the barrel with the other bone screw hole of the "pair." The second hole may then be prepared in the same manner as the first. After drilling is complete, the drill guide may be lifted off the plate and similarly aligned with another "pair" of bone screw holes. Since the location post is not affirmatively retained within the end hole, unwanted movement of the plate is minimized during removal of the drill guide from the plate.

Figure 4:
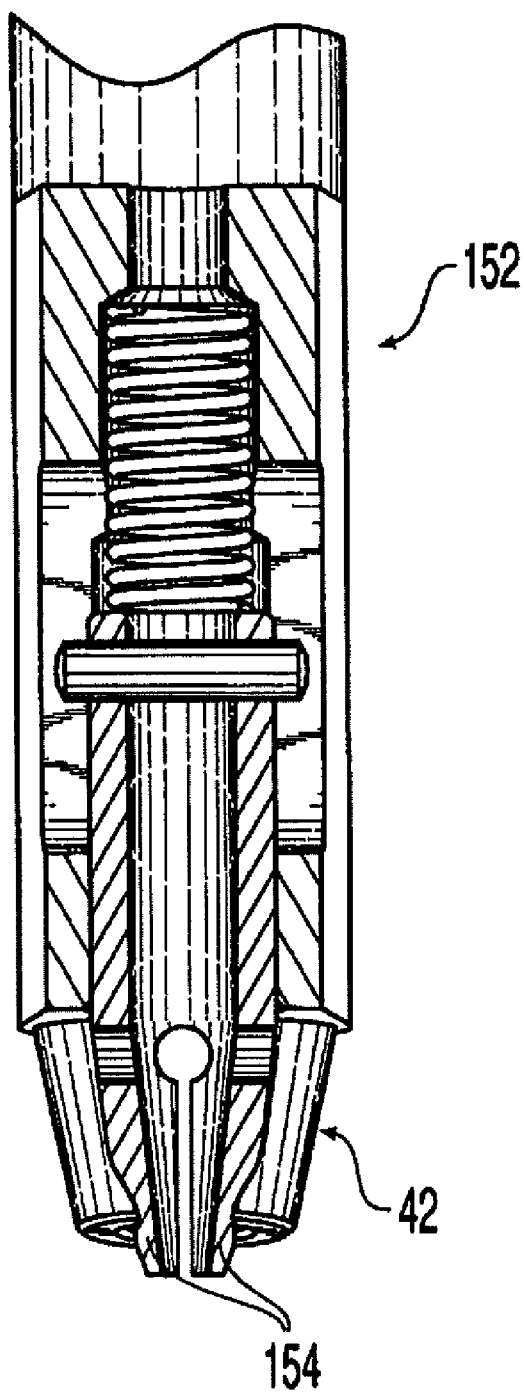
FIG. 4 is a cross sectional detail view of an embodiment of the drill guide of FIG. 1 incorporating an alternative plate-retaining feature.
Figure 10:
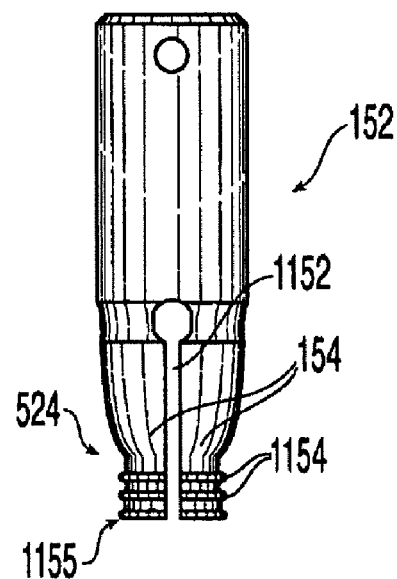
FIG. 10 is a side view of an alternative embodiment of the location post of FIG. 4.

In an alternative embodiment, illustrated in FIGS. 4 & 10, the plate aligning mechanism 50 may have a location post 152 with a plate-retaining feature comprising a plurality of axial slots 1152 which may form a plurality of resilient fingers 154. This arrangement may allow the plate aligning mechanism 50 to axially retain the bone plate which may allow the surgeon to use the drill guide 10 as a plate holder. As the location post 152 is inserted into the slot end-hole 72 of the plate 70, the fingers 154 are compressed together, causing the them exert an expansion spring force against the inner surface of the end-hole 72 in the bone plate, thereby axially locking the drill guide 10 to the plate 70. Although the expansion force may be sufficient to axially lock the drill guide to the plate, the location post may remain rotatable within the hole 72, thus allowing the guide barrel 40 to be swiveled to align with a pair of bone screw holes 74R, L, as described with respect to the previous embodiment.

To increase the locking strength of the location post 152 within the slot end-hole 72 of the bone plate 70, the resilient fingers 154 may comprise one or more circumferential ridges 1154 which may engage the inner surface of the slot end-hole 72. This arrangement may be particularly effective where the slot end-hole 72 is threaded, because the circumferential ridges may engage a portion of the slot end-hole threads.

Figure 13:
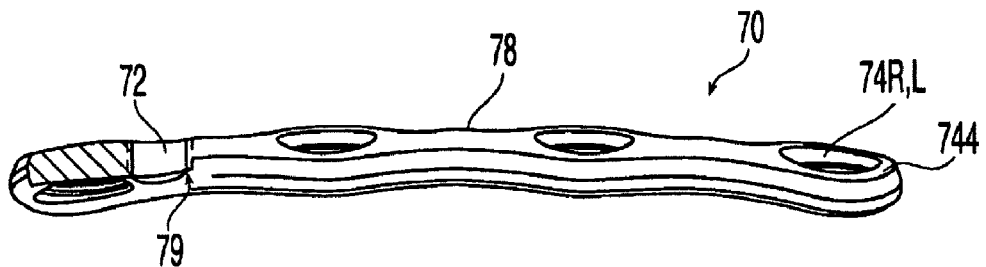
FIG. 13 is a side sectional view of the bone fixation plate of FIG. 2A.
Figure 18:
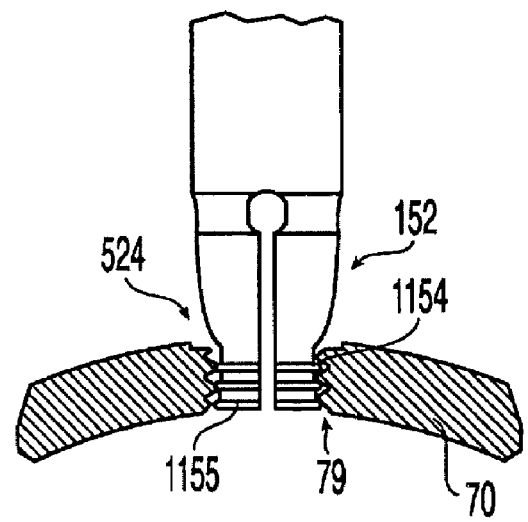
FIG. 18 is a cross-sectional view of the location post of FIG. 10 engaged with the plate of FIG. 2A.
Figure 19:
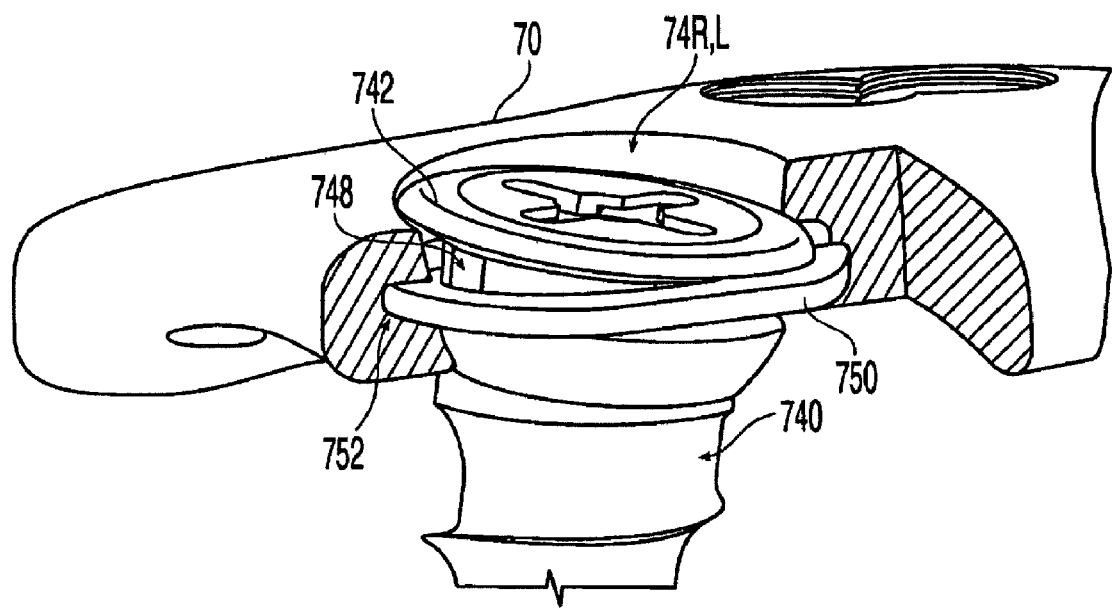
FIG. 19 is a perspective cutaway view of an exemplary bone screw engaged with a bone screw hole of a plate having a locking clip.

Further, as illustrated in FIG. 18, an end portion 1155 of each of the locking post fingers 154 may comprise a circumferential ridge that may engage an underside surface (FIGS. 13 & 18) of the bone plate 70 when the post is engaged with the slot end hole 72.

This locking post arrangement of FIGS. 4 & 10 may eliminate the need for a separate tool to place and hold the bone plate in place within the surgical site. The remaining features of the drill guide of this embodiment are the same as that described in relation to the previous embodiment. Thus, once the locking post 152 is engaged with the slot end hole 72, the guide barrel 40 of this embodiment may be aligned within a targeted screw hole 74R, L and used with an awl, tap and drill in the same manner as the drill guide of FIG. 1. After use, however, the drill guide may be disconnected from the plate by pulling up on the handle with sufficient force to disengage the resilient fingers 154 from the plate slot end-hole 72.

Figure 2A:
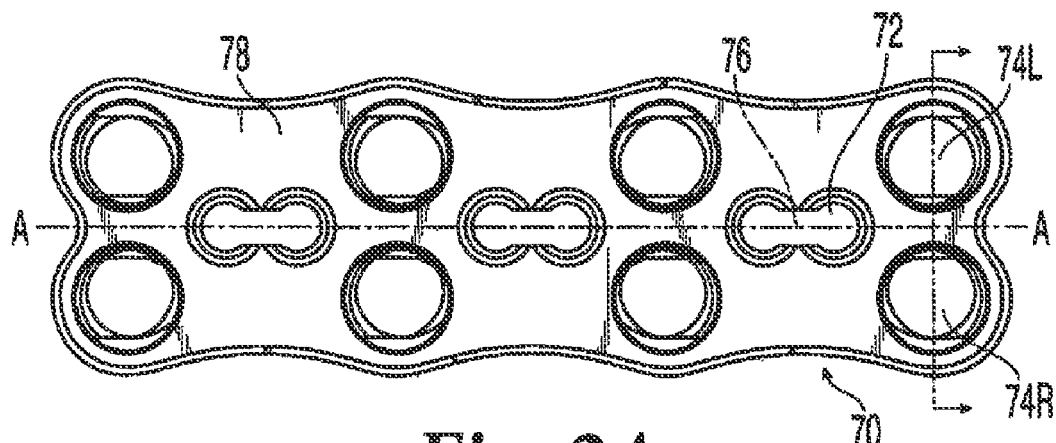
FIGS. 2A, 2B and 2C are top, side cross section and end cross section views, respectively, of the bone plate of FIG. 1.
Figure 2B:
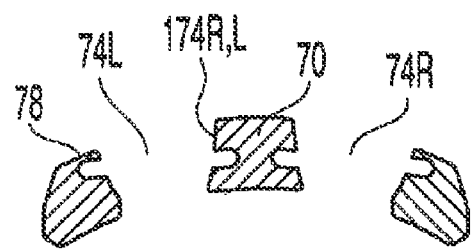
Figure 2C:
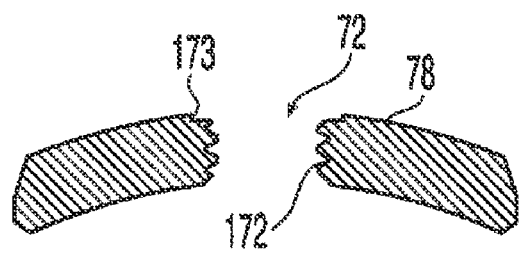

With reference to FIG. 2A, an exemplary bone plate 70 is illustrated. The plate 70 may have a plurality of "pairs" of bone screw hoes 74R, L disposed along the length of the plate, and each "pair" of bone screw holes may correspond to a pair of bone screws used to engage a single vertebra. The bone screw holes 74R, L may have at least an upper portion 174R, L (FIG. 2B) that is conical in cross section, and this portion may be configured to receive the conical nose portion 42 of guide barrel 40. A slot 76 may be provided between successive bone screw hole "pairs," and this slot may take the shape of a "dog-bone" (i.e. it may comprise a slot with an expanded portion 72 located at either end). In the illustrated embodiment the expanded portions are circular holes 72 (FIG. 2C). Each hole 72 may be configured to receive the location post 52 (FIGS. 3A, 3B) of drill guide 10 to couple the drill guide and bone plate. The slot 76 may have a longitudinal axis that is substantially parallel to the longitudinal axis "A-A" of the plate 70, and in the illustrated embodiment the slot is also centered on the plate axis. The inner surface 172 of each end hole 72 may be smooth, threaded or ribbed, and a counterbore 173 may also be provided at the top of the hole to provide a flat surface for embodiments of the plate 70 in which the plate top surface 78 is curved. The end holes 74 may have parallel sides, or the holes may be fully or partially conical in cross-section. It is noted that the end-holes may be provided in any appropriate configuration or combination of configurations known in the art.

Figure 3A:
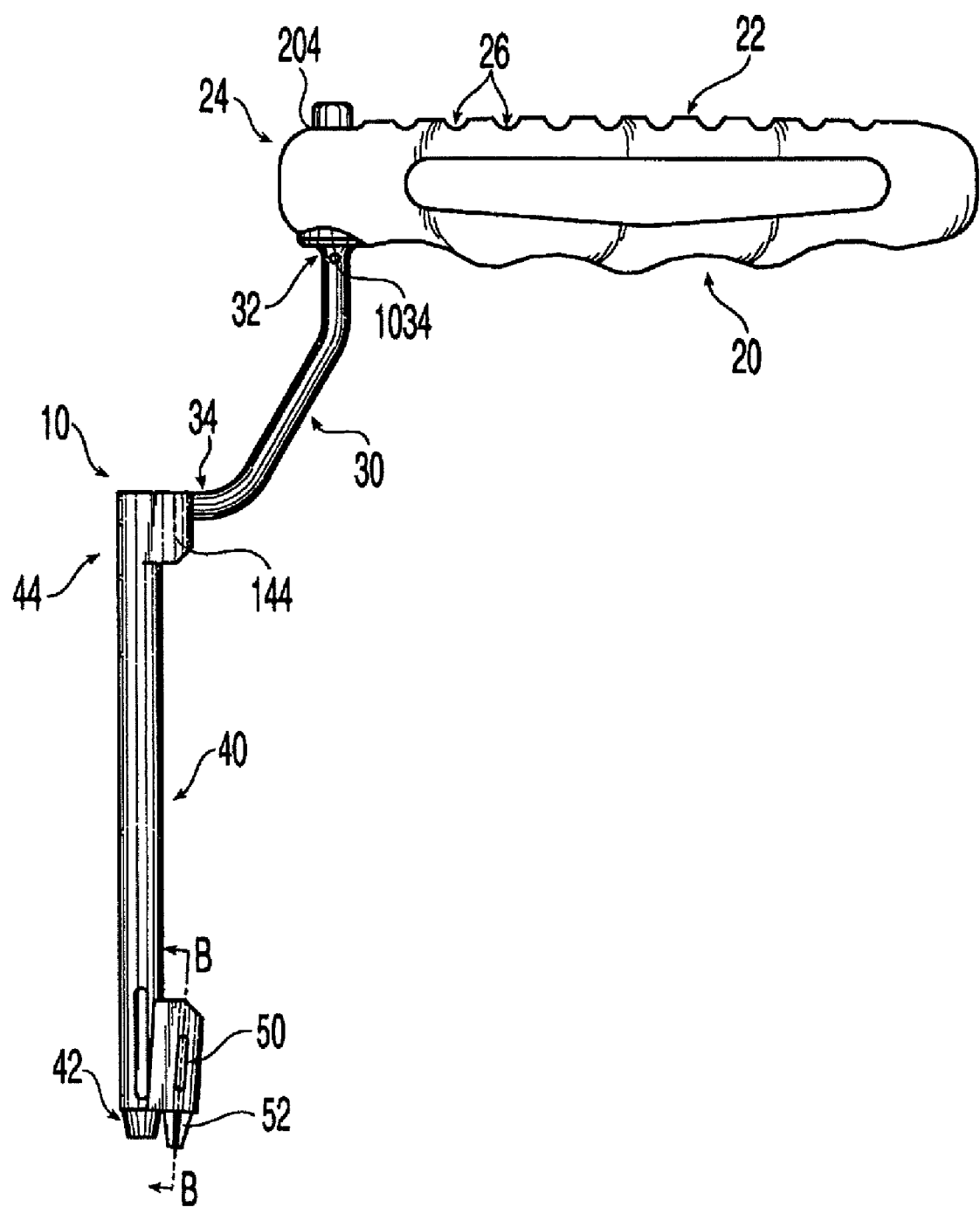

As shown in FIG. 3A, the drill guide 10 may have a handle 20 with a gripping portion 22 and an extension-engaging portion 24. The gripping portion 22 may assume any appropriate configuration, and in the illustrated embodiment is provided with an elongated ergonometric shape having a plurality of surface slots 26 to maximize gripping by the user during operation. The extension-engaging portion 24 may be configured to receive the proximal extension 32 of a handle extension element 30 which itself may have a distal extension 34 that engages the drill guide barrel 40. The extension-engaging portion 24 of the handle may further comprise a swivel assembly 28 to allow the handle 20 to be swiveled about the extension 30 and the guide barrel 40 during use. This swiveling function may allow the user to adjust the rotational position of the handle 20 with respect to the guide tube 40 to provide the most convenient approach of the device to the bone plate 70 and to the surgical site, and also may allow the handle to be rotated away from the work site once the plate 70 has been placed on the bone and the drill guide 10 has been positioned on the plate. The swivel assembly 28 may further be provided with a selective locking feature to allow the user to lock the handle in a desired rotational position with respect to the handle extension 30 and guide barrel 40.

Figure 5A:
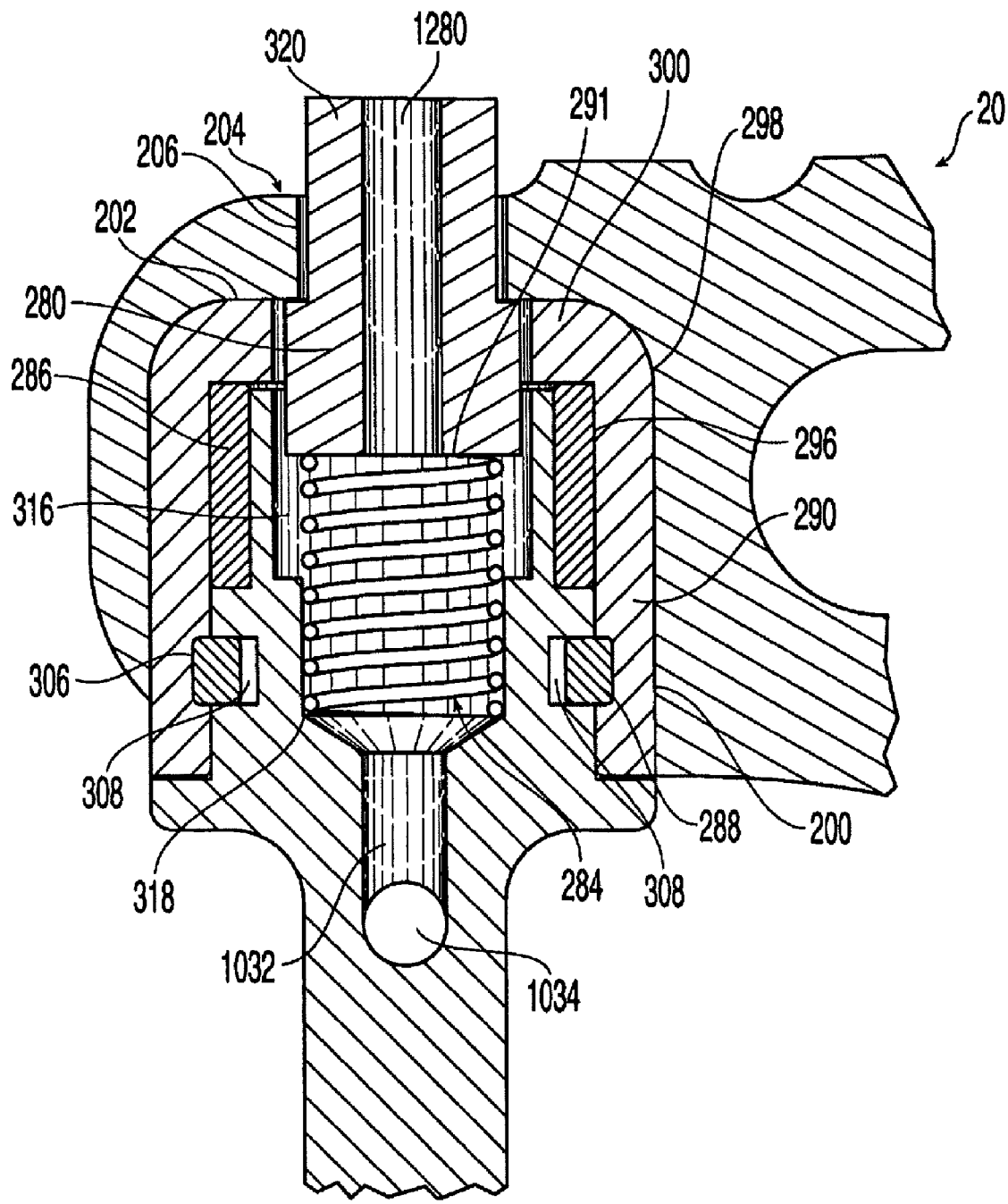
FIGS. 5A and 5B are cross-sectional detail and exploded views, respectively, of the swivel handle mechanism of the drill guide of FIG. 1.
Figure 5B:
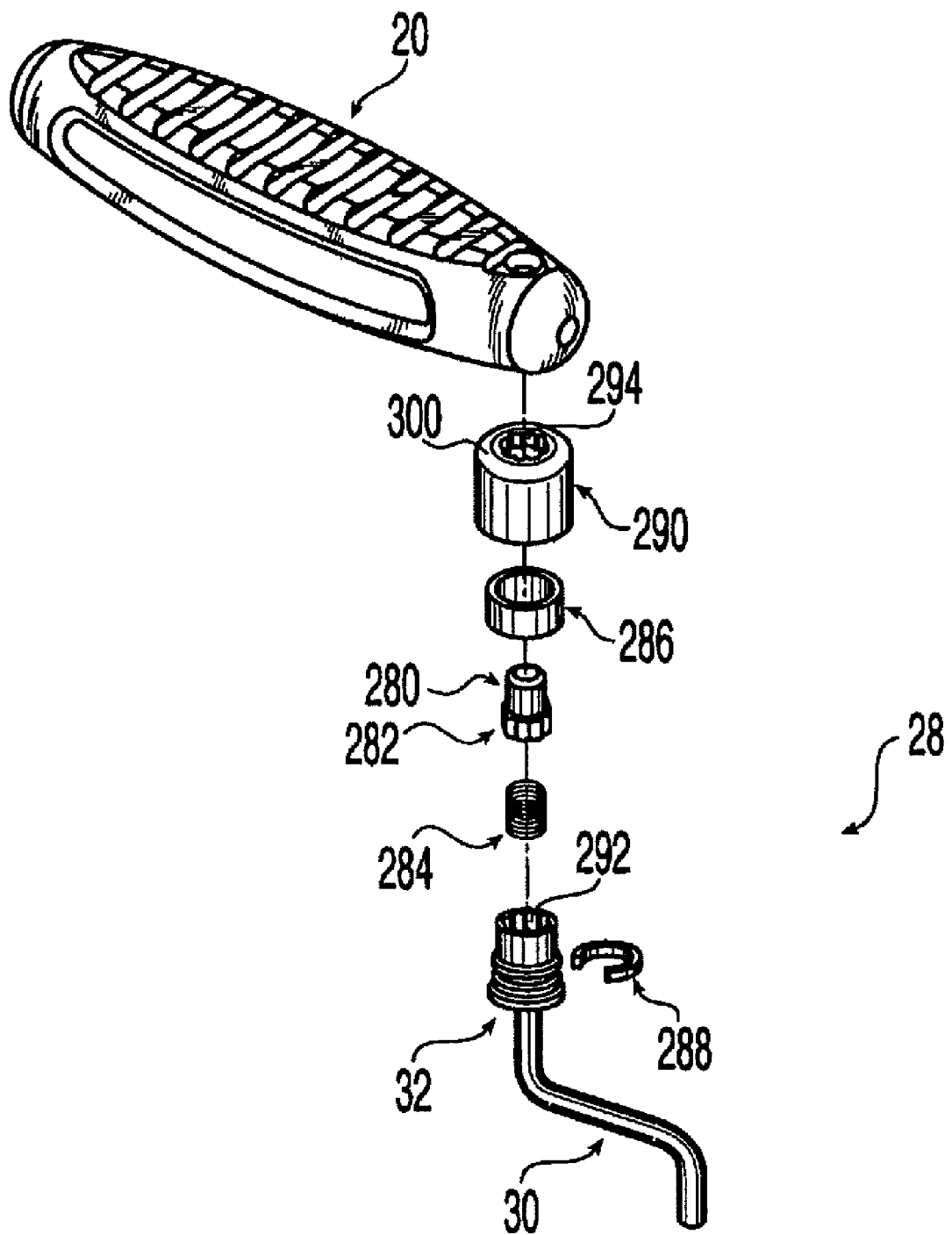

Referring to FIGS. 5A-6B, the swivel assembly 28 will be described in more detail. The handle swivel assembly 28 may comprise a button cam 280 having a set of radial detents 282 (FIG. 5B), a cam spring 284, a bearing 286, a locking element 288 and a handle sleeve 290. The radial detents 282 may be configured to engage corresponding sets of detent grooves 292, 294 (FIG. 5B) formed in the handle proximal extension 32 and the handle sleeve 290, respectively. The handle sleeve 290 may have inner and outer surfaces 296, 298, with the outer surface 298 configured to be received within a bore 200 in the extension engaging portion 24 of the handle 20. The handle sleeve 290 may further comprise an upper shoulder region 300 configured to abut an inner axial stop surface 202 of the handle 20. The upper shoulder region 300 may comprise a series of radially-disposed detent grooves 294 configured to receive radial detents 282 of button cam 280. The inner surface 296 of the handle sleeve 290 may further be configured to receive the proximal handle extension 32 for sliding rotational movement therein. A bearing 286 may be provided between the proximal handle extension 32 and the handle sleeve inner surface 296 to facilitate smooth rotational movement between the pieces to reduce the amount of force required to rotate the handle about the handle extension and to reduce wear of the components. The handle sleeve 290 and proximal handle extension 32 may be axially locked together by means of a locking element 288 positioned within respective radial grooves 306, 308 formed in the sleeve 290 and handle extension 32, respectively. In the embodiment of FIGS. 5A & 5B, the bearing 286 may comprise a sleeve element fabricated from a polymer, such as Teflon, PEEK (polyether-ether-ketone), or other suitable bearing material. Likewise, the locking element 288 may comprise a C-shaped clip formed of Teflon, PEEK or other suitable material. Using non-metallic bearing and locking elements 296, 288 may increase the useful life of the swivel assembly which, along with the other components of the drill guide 10, may undergo high temperature steam sterilization after each use. This exposure to steam, coupled with the difficulty in completely drying the swivel assembly components after exposure, may lead to corrosion of assembly components. In particular, galvanic corrosion of individual components may occur where the assembly components are made of different metals and are not separated by a non-metallic material. Thus, a non-metallic bearing and a non-metallic locking clip may be provided. It is noted that the use of a non-metallic bearing and locking clip material may provide the advantage of preventing galvanic corrosion between the metallic components of the swivel assembly 28 when these components are subjected to the high-moisture environment of the sterilization process. Such corrosion is undesirable because it may reduce the efficiency of the swivel assembly after only a few uses due to the presence of corrosion particles between bearing surfaces.

To further facilitate minimize the chance for corrosion of the swivel assembly pieces, drain holes 1280, 1032 may be provided in the button cam 280 and proximal extension 32, respectively to facilitate drainage of any condensation remaining after sterilization of the drill guide 10. Hole 1032 may exit the handle extension 30 at port 1034, thus providing a drainage path between the top portion of the button cam 280 and the handle extension 30. High pressure air may also be applied to either end of the drainage path to blow out remaining fluid.

Figure 6A:
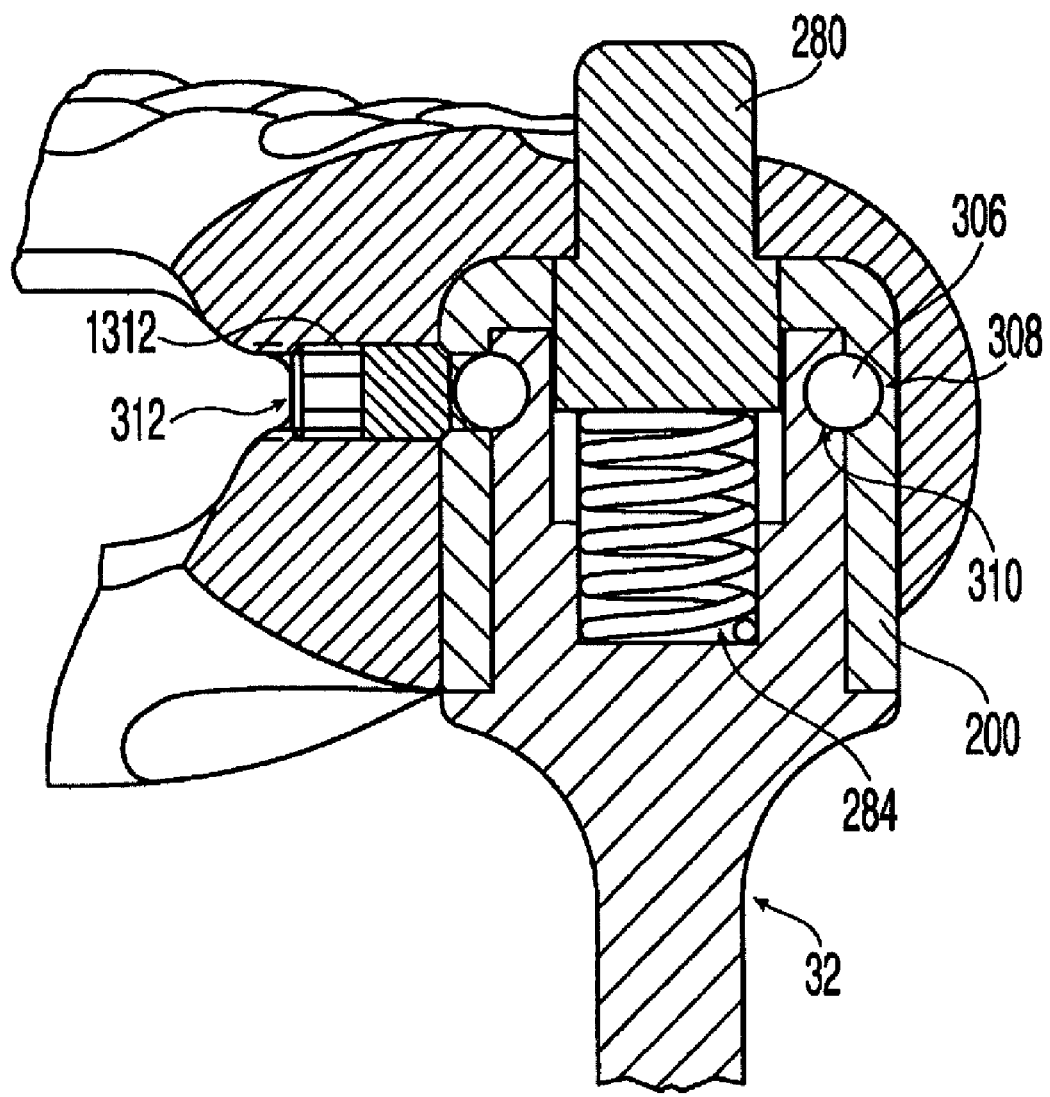
FIGS. 6A and 6B are cross-sectional detail and exploded views, respectively, of an alternative embodiment of the swivel handle mechanism of FIGS. 5A and 5B.
Figure 6B:
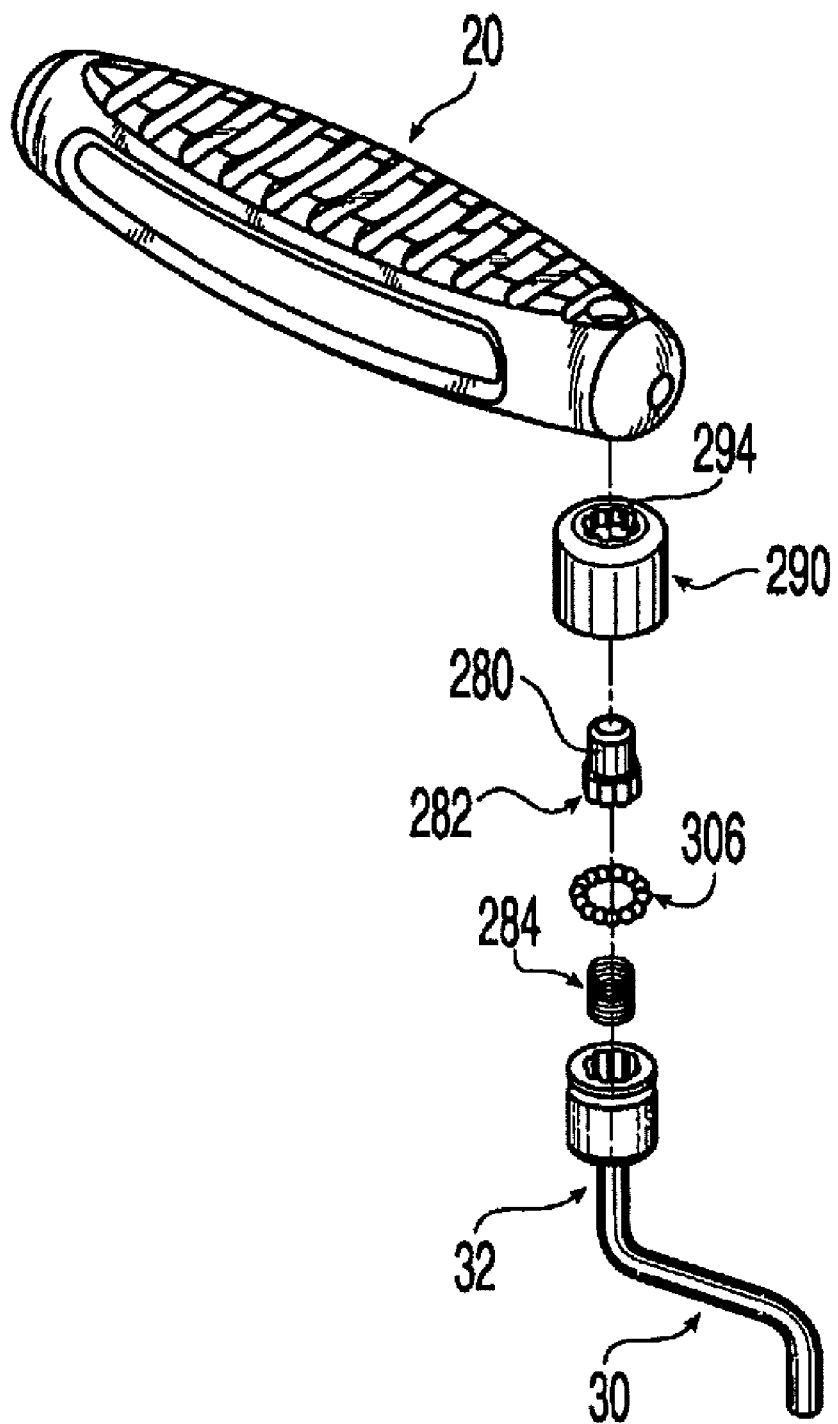

In an alternative embodiment, shown in FIGS. 6A & 6B, the bearing may comprise a series of balls 306 configured to move within corresponding circumferential grooves 308, 310 in the handle sleeve 200 and proximal handle extension 32, respectively. With the balls 306 in place within the grooves 308, 310, the handle sleeve 200 may further be axially locked to the proximal handle extension 32. To facilitate introduction of the balls 306 into the grooves 308, 310, the handle 20 may have an axial bore 1312 through which the balls may be loaded between the grooves 308, 310 once the proximal handle extension 32 has been fit within the handle sleeve 200. A set screw 312 may then be threaded into the bore 1312 to prevent the balls 306 from escaping. The balls 306 may be made from stainless steel, chrome plated steel, or other metal (coated or uncoated) suitable for use as a bearing material. Alternatively, the balls 306 may be made from a suitable non-metallic material, such as a polymer (e.g. ultra-high molecular weight polyethylene). The swivel assembly of this embodiment further may incorporate a drain hole arrangement similar to that described above in relation to FIGS. 5A and 5B, to reduce or eliminate corrosion of the swivel assembly pieces.

Referring again to FIGS. 5A & 5B, the proximal extension 32 of handle 30 may comprise first and second axial bores 316, 318 configured to receive the button cam 280 and the cam spring 284, respectively. When assembled, cam spring 284 may be positioned within the second bore 316 and may abut the lower surface 291 of the button cam 280 to bias the button upwardly toward a top surface 204 of the handle 20. The handle 20 may have a second bore 206, positioned coaxial with the bore formed by the circumferential inner surface 296 of the handle sleeve 290, and may be configured to receive the button portion 320 of the button cam 280 therethrough, so that the upward bias of the cam spring 284 may force the button portion 320 up through the handle portion so that it protrudes above the top surface 204 of the handle 20. Thus, the button cam 280 may be conveniently thumb-actuated by the user while a grip is maintained on the drill guide handle 20.

In the unactuated "neutral" position, the handle 20 is axially and radially locked to the handle extension 30 via the engagement of the radial detents 282 of the button cam 280 with detent grooves 292, 294 of the proximal extension 32 and the handle sleeve 290, respectively. To rotationally unlock the handle 20 from the handle extension 30 to allow the handle to be swiveled with respect to the remainder of the drill guide assembly, button cam 280 is pressed downward against the bias of cam spring 284. This downward axial movement of the button cam 280 within the first bore 316 of the proximal extension 32 may cause the radial detents 282 to move out of engagement with the detent grooves 294 of the handle sleeve 290 thus rotationally decoupling the handle 20 from the handle extension 30, and allowing handle member 20 to be rotated with respect to the handle extension 30. Releasing pressure on the button cam 280 causes cam spring 284 to return detents 282 of button cam 280 into engagement with detent grooves 294 of handle sleeve 290 to again prevent rotation of handle member 20 in relation to handle extension 30.

As shown in FIG. 3A, the handle 20 may be offset from drill guide barrel 40 by offset handle extension 30, thus allowing greater visibility and access to bone plate 70 and the vertebra. Distal extension 34 may be mechanically attached to the proximal portion 44 of drill guide barrel 40 at an extension receiving section 144, for example by welding, brazing, a threaded connection, friction fit or pinned connection. Extension receiving section 144 may comprise a bore into which a cylindrical portion of distal extension 34 is inserted, or handle extension 30 may be associated with guide barrel 40 in any appropriate manner. For example, the distal extension 34 may comprise a bore configured to engage at least a portion of the outer surface of the guide barrel proximal portion 44, and which may be attached by welding, brazing, a threaded connection or friction fit. Alternatively, the handle extension 30 may be formed integrally with the guide barrel 40.

Figure 7:
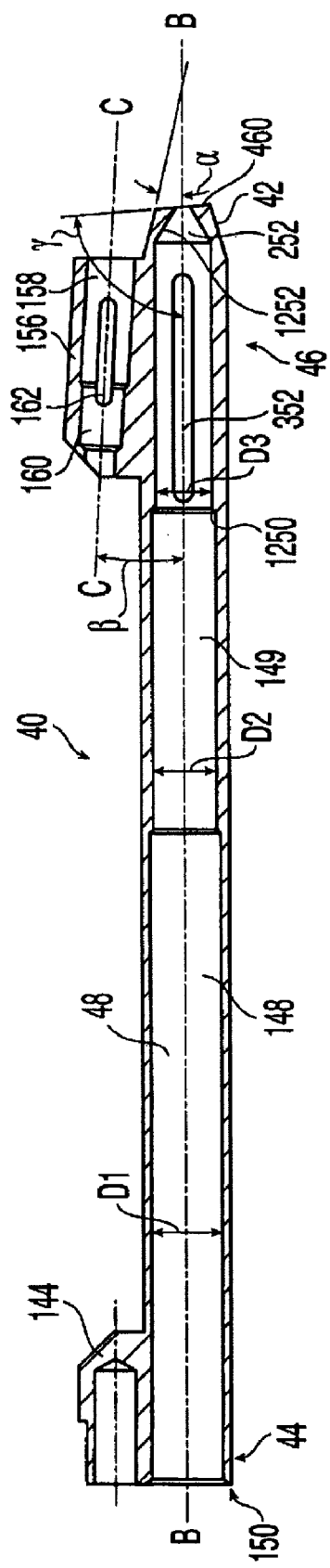
FIG. 7 is a cross-sectional view of the guide barrel portion of the drill guide of FIG. 1.
Figure 14A:
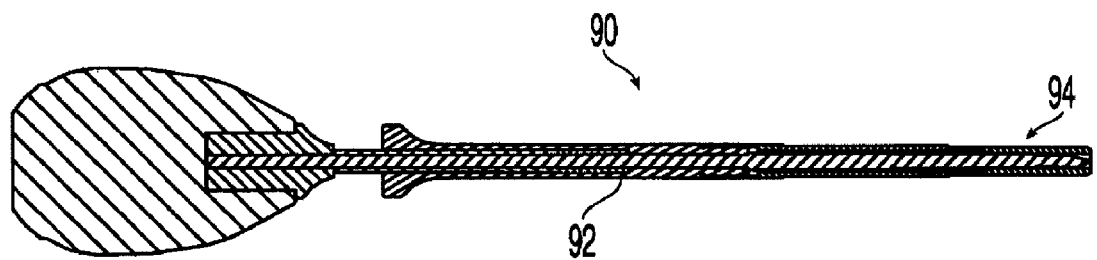
FIGS. 14A and 14B are side and cross-sectional detail views, respectively, of an awl for use with the drill guide of FIG. 1.
Figure 14B:
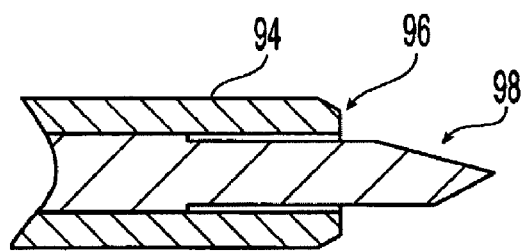

Referring to FIG. 7 an exemplary guide barrel 40 is illustrated. The drill guide barrel 40 may have a proximal handle engaging end 44 and a distal plate engaging end 46. The guide barrel may further comprise a longitudinal bore 48 having a bore axis "B-B." The guide barrel bore 48 may be configured and dimensioned to slidingly receive therethrough a number of bone hole preparation tools, such as an awl, tap and/or drill. The guide barrel bore 48 may comprise a proximal portion 148 having a first diameter "D1" and a distal portion 149 having a second diameter "D2," and the first diameter "D1" may be greater than the second diameter "D2." Where the drill guide 10 is used with an awl 90 (FIGS. 14A, B), "D1" may be sized to accept a proximal middle portion 92 of the awl, and "D2" may be sided to slidingly accept a distal barrel portion 94 of the awl. Furthermore, the guide barrel distal end 46 may have a conical inner surface 1252 configured to receive the conical nose portion 96 of the awl barrel portion 94.

Figure 15:
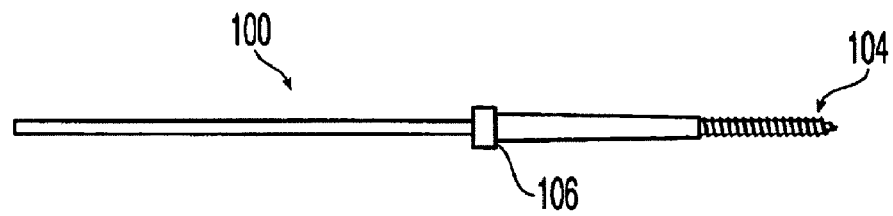
FIG. 15 is a side view of a tap for use with the drill guide of FIG. 1.

The proximal handle engaging end 44 of the barrel 40 may have an end face 150 that may function as a stop surface for the drill bit 80, which may limit the total depth of penetration of the drill tip 88 into the bone, thus limiting the ultimate bone hole to a predetermined depth. In the illustrated embodiment, end face 150 may cooperate with shoulder 810 on drill bit 80 (FIG. 11) to perform this depth limiting function.

Where the drill guide 10 is used with a tap 100 (FIG. 15), the guide barrel bore 48 may comprise a stop surface 1250 configured to engage a corresponding shoulder 106 of tap 100. These corresponding stop surfaces may cooperate to limit the distance which thread tapping surface 104 may penetrate into the bone hole.

The drill guide barrel distal end 46 may further have a conical nose portion 42 configured and dimensioned to be received within the conical bone screw holes 74R, L of bone plate 70. In one embodiment, the conical nose portion may have a taper angle α configured to substantially match the taper of the corresponding conical portion 174R, L of bone screw hole 74R, L. Alternatively, the taper angle α may be greater than or less than that of the bone screw hole conical portion 174R, L. It is noted that any appropriate taper angle α may be provided, as long as the taper functions to center the guide barrel within the bone screw hole to precisely align the barrel with the bone screw hole to ensure the appropriately placed and angled hole is drilled in the underlying bone. In one embodiment, the taper angle α of the conical nose portion may be about 12 degrees. Furthermore, the end surface 460 of the guide barrel distal end 46 may be non-orthogonal with respect to the guide barrel bore axis "B-B," so that when the conical nose portion of the guide barrel is received within the bone screw hole, the end surface 460 is substantially parallel to the underside surface of the bone plate (i.e. to reduce or eliminate the chance that any portion of the guide barrel might extend through the bone screw hole and contact the underlying bone). In one embodiment, the angle γ formed between the end surface 460 and the guide bore axis "B-B" may be about 85 degrees. Providing an angled end surface 460 further may allow the drill guide conical nose portion 42 to engage a portion of the bone screw hole 74R, L even where the conical nose portion 42 is not precisely aligned with the tapered portion 174 of the bone screw hole (i.e. where the axis "B-B" of the drill guide barrel is not coaxial with the trajectory of the bone screw hole). This may be the case when the surgeon is initially aligning the guide barrel with the bone screw hole, or it may also be where the surgeon purposely aligns the guide barrel out of alignment with the bone screw hole trajectory (for example, to align the bone screw with an area of higher integrity bone than exists at the point directly in line with the bone screw hole trajectory).

The angle γ may also be selected to ensure engagement between the guide barrel conical nose portion 42 and the bone screw hole 74R, L only where the guide barrel 40 axis and the screw hole trajectory are misaligned within a certain predetermined range. Thus, in the illustrated embodiment, a portion of the end surface 460 of the nose portion 42 will engage a portion of the bone screw hole 74R, L only up to a predetermined range of misalignment of about 5 degrees (the complement of the angle between the end surface 460 and axis "B-B"). This predetermined range may be selected by adjusting the angle γ to ensure that the bone screw 740 will not ultimately be inserted too far out of alignment with the bone screw hole trajectory (since such misalignment may reduce the effectiveness of the engagement between the bone screw and the plate). The angled end surface 460 feature thus provides the surgeon with immediate feedback to ensures the ultimate bone screw alignment will be within the predetermined range (i.e. if the end surface 460 is engaged with the bone screw hole 74R, L, then the hole is within the range; if the end surface 460 does not engage the bone screw hole 74R, L, then the hole alignment is outside the range and should be adjusted).

Figure 11:
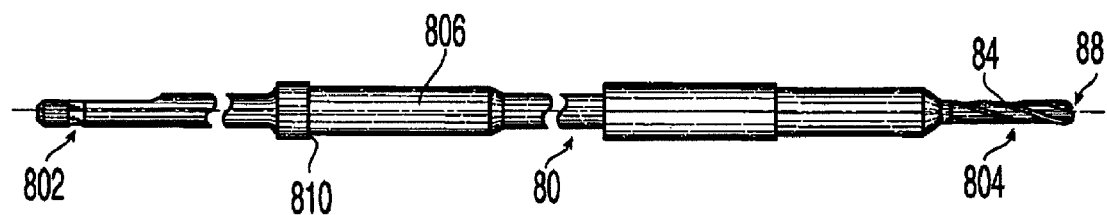
FIG. 11 is a side view of an exemplary drill bit for use with the drill guide of FIG. 1.

Corresponding to this conical nose portion 42, the guide barrel bore 48 may comprise an internal reduced diameter portion 1252 that has an inner diameter less than the diameter "D2" of bore distal portion 149, and which is only slightly greater than the outer diameter of the fluted portion 84 of drill bit 80 (FIG. 11). This reduced diameter portion 1252 of bore 48 may also serve as a stop surface for the tool to prevent the tool from penetrating farther into the bone than desired. The reduced diameter portion 1252 may also act as bearing surface to support and guide the fluted portion 84 of the drill. It may also serve to reduce the amount of drilling debris drawn up into the drill guide during use.

Figure 8:
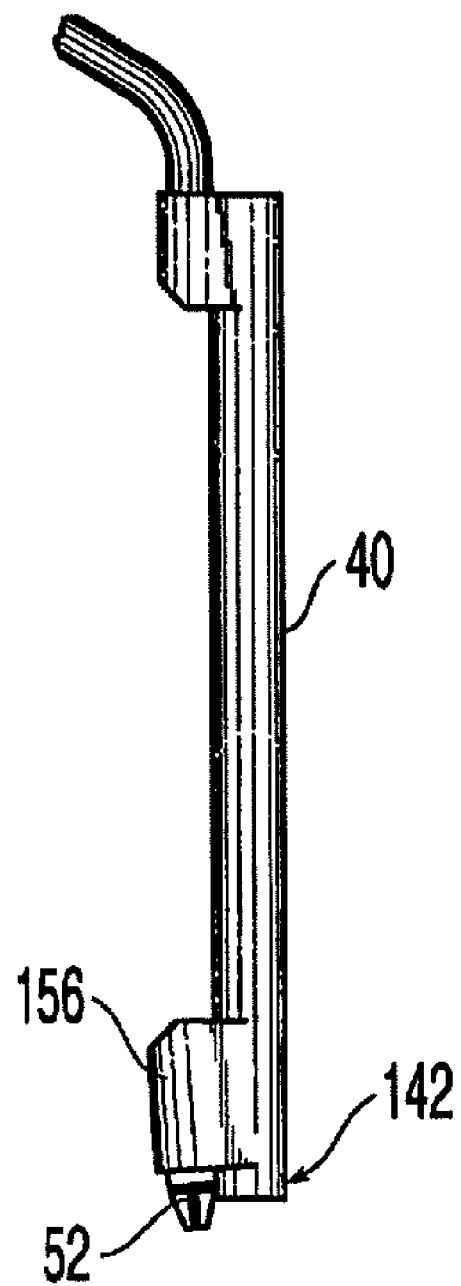
FIG. 8 is a side view of an alternative embodiment of the guide barrel portion of FIG. 7.

In an alternative embodiment, shown in FIG. 8, guide barrel 40 may have a distal nose portion 142 having a non-conical end portion. With this alternative nose design, the guide barrel distal end may not be received within the bone screw hole, thus the surgeon may not use the bone screw hole to automatically align the guide barrel with the bone screw hole. The surgeon may, however, use one of the cavity forming tools to precisely align the drill guide barrel with the targeted bone screw hole. For example, when using the awl of FIGS. 14A, B, the awl barrel 94 may be placed through the guide barrel 40 until the conical nose portion 96 extends beyond the guide barrel distal end 46 and engages the conical portion 174R, L of the targeted bone screw hole 74R, L. The rotational position of the drill guide barrel 40 may then be adjusted to nest the tapered nose 96 of the awl within the conical portion 174R, L of the bone screw hole. The awl tip 98 may then be used to form an entry hole through the cortex of the bone in the desired location. Thereafter, the drill 80 (FIG. 11) and tap 100 (FIG. 15) may simply be aligned with the entry hole.

Since the flat-nosed end 142 of the guide barrel is not engageable with a bone screw hole 74R, L, the location post 52 may be fixed within the guide barrel housing 156, rather than being slidable and spring biased as with the previously described embodiments. The post 52 may be fixed within the barrel using any appropriate joining method (e.g. brazing, welding, adhesive), or it may be formed as an integral part of the housing.

Since the nose portion 142 of the guide barrel of this embodiment does not have a reduced-diameter conical nose portion (and thus the attendant reduction in inner bore diameter at the guide barrel nose), the guide barrel bore may allow placement of a bone screw 740 and screwdriver therethrough, in addition to the awl, tap and drill of the previous embodiment.

Referring again to FIG. 7, the distal end of guide barrel 40 may further comprise a viewing slot 352 disposed in the barrel wall. This viewing slot may be used by the surgeon to visually verify the location of the distal tip of a tool inserted through the guide barrel (for example, tip 88 of drill bit 80). In the illustrated embodiment the viewing slot 352 comprises an elongated channel having an axis parallel to the axis of the guide barrel bore 48. The viewing slot may, however, assume any appropriate shape, configuration, or orientation known in the art.

The distal end of guide barrel 40 may also comprise a housing 156 which encloses a plate engaging mechanism 50. This housing 156 may be formed integrally with the guide barrel or it may be a separate piece that is attached by welding, brazing, adhesive, etc. The housing 156 may comprise a bore 158 configured to slidably receive a location post 54 of the plate engaging mechanism 50. The bore may have an axis "C-C" that forms an acute angle β with respect to longitudinal axis "B-B" of the guide barrel. When the drill guide is installed on bone plate 70, the plate engaging mechanism 50 may be oriented so that axis "C-C" is substantially perpendicular to the top surface 78 of the bone plate 70. Thus, angle β may be the angle at which the awl, tap and drill will be inserted into the bone, and so it may also be the angle at which the bone screws will ultimately be installed in the bone. To ensure proper engagement between the bone screw 740 and the screw hole, 74R, L, angle β may be selected to correspond to the trajectory of the associated bone screw hole 74R, L in the plate 70, which in an exemplary embodiment is about 4 degrees.

The housing 156 may further comprise a slot 160 oriented substantially parallel to axis "C-C" and configured to receive a pin 162 used to retain location post 54 within the housing 156. This feature will be described in more detail below.

Figure 3B:
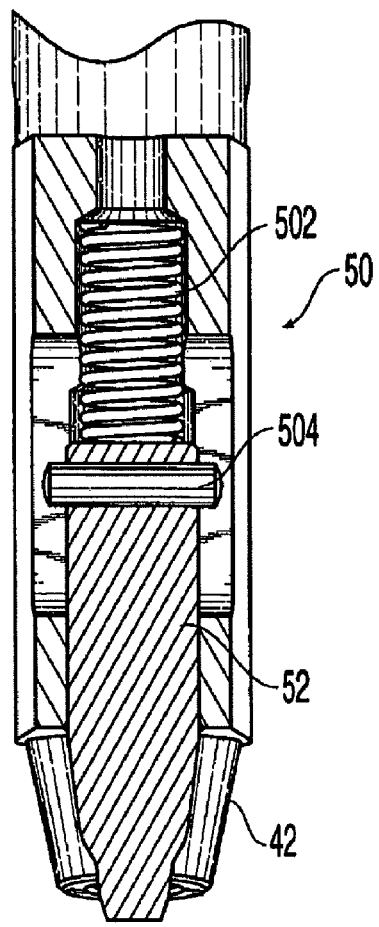
Figure 3C:
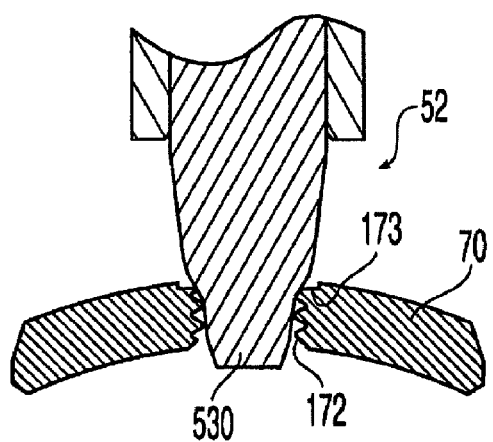
FIG. 3C is a cross sectional view of the drill guide of FIG. 1 engaged with the plate of FIG. 2A.

Referring to FIG. 3B, plate engaging mechanism 50 will be described in greater detail. Plate engaging mechanism 50 is designed to stabilize the drill guide 10 on the bone plate 70 and to provide a pivot point about which the guide may be rotated so as to bring the guide barrel 40 into alignment with a targeted pair of bone screw holes 74R, L, thus allowing two bone screw holes to be drilled with only a single placement of the drill guide on the bone plate.

Figure 9:
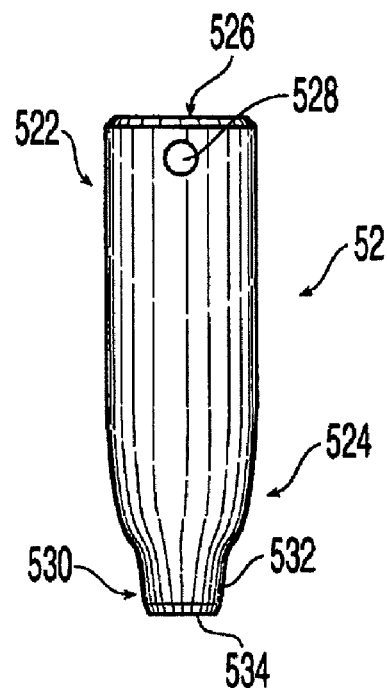
FIG. 9 is a side view of the location post of the drill guide of FIG. 1.

The plate engaging mechanism 50 may comprise a location post 52 (FIG. 9) configured to cooperate with a slot-end hole 72 of a bone plate to stabilize the drill guide on the bone plate. The location post 52 may have a proximal end 522 configured to slide within bore 158 of guide barrel housing 156 (FIG. 7), and a distal end 524 configured to cooperate with slot-end hole 72 of bone plate 70. A spring element 502 may be provided within guide barrel housing 156 and may be configured to engage the location post on its proximal end surface 526 to axially bias the location post 52 in the distal axial direction (i.e. in the direction of the bone plate 70). The location post 54 may be axially retained within the housing bore by a pin 504 which may be passed transversely through a bore 528 in the proximal portion of the post 52 and which may also engage slot 162 of the guide barrel housing 156 (FIG. 7). Thus, when the plate engaging mechanism is assembled, the spring 502 may force the location post to move in the axial distal direction until the pin 504 abuts the distal most end of the slot 162 in the housing 156, whereupon further axial movement of the post 52 is prevented.

The distal end of location post 52 may comprise a nose section 530 configured to sit within the slot end-hole 72 of the bone plate 74. In the illustrated embodiment, the nose section 530 has rounded sides 532 and a flat end 534. In this embodiment, the rounded sides 532 are configured to contact the inner surface 172 of slot end-hole 72 to seat the post within the hole, but without axially retaining the post therein (i.e. lifting the drill guide up off the bone plate will not cause the plate to move upward with the drill guide).

This configuration of the nose section 530 and the slot end-hole 72 may allow the location post 52 to "toggle" within the hole, thus allowing the surgeon to adjust the drill guide barrel 40 trajectory slightly within the targeted bone screw hole 74R, L while still maintaining the connection between the location post 52 and the plate end-hole 72. This "toggling" feature may the surgeon to customize the trajectory of the hole (i.e. alter it from the trajectory of the bone screw hole 74R, L) that will be drilled into the bone, thereby customizing the trajectory of the bone screw that will be placed in the hole. This feature may provide the surgeon with an important degree of flexibility the bone underlying the plate is of varying integrity. For example, where the area of bone directly in line with the bone screw hole 74R, L is of sub-standard integrity, a slight adjustment in the guide barrel trajectory (while still maintaining the nose 42 engaged with the bone screw hole 74R, L) may allow the surgeon the option of placing the hole (and thus the screw) within an immediately adjacent higher integrity area of bone.

This "toggling" feature may also allow the surgeon greater flexibility in drilling holes in vertebra that may be difficult to access, such as the cervical vertebra C1 through C3, and C7. Anterior access to these vertebra may be partially obstructed by the chin (C1-C3) or the sternum (C7), and thus, it is an advantage to allow the surgeon the option of adjusting the guide barrel trajectory to avoid the obstruction, while maintaining the contact between the plate slot end hole 72 and the location post 54.

The nose section may be used with slot end-holes having various inner surface configurations (e.g. smooth, threaded, ribbed, conical, etc.). This configuration minimizes the chance that the bone plate position on the bone will be affected when the drill guide is disengaged from the plate (e.g. when the drill guide is repositioned on the bone plate to access a second pair of bone screw holes).

The spring-biased feature of the location post 52 allows the drill guide barrel 40 to assume a "neutral" position with respect to the bone plate 70 when the location post is received within the slot end-hole 72. In this "neutral" position, the nose portion of the guide barrel is axially offset from the top surface of the bone plate 70, and thus may then be freely pivoted about the location post to position the barrel 40 in alignment with a right or left bone screw hole of a targeted bone screw hole pair 74R, L. Final alignment of the guide barrel 40 with the bone screw hole 74R, L may then be achieved by pressing downward on the drill guide handle 20, thus compressing the location post spring 502, and allowing conical nose portion 42 of the guide barrel 40 to fit precisely within the targeted bone screw hole 74. Bone hole preparation tools may then be introduced through the barrel. Once bone hole preparation is complete for the first of the pair, the downward force on the handle may be reduced, thus allowing the spring 502 to move the drill guide up and away from the plate 70. The guide barrel may then be pivoted about the location post to align with the second bone screw hole of the pair.

An alternative location post design is shown in FIG. 10, in which distal portion 524 comprises a plate-retaining feature, which is illustrated as a plurality of resilient fingers 154 configured to engage the slot-end hole 72 of the bone plate 70. This arrangement may allow the plate aligning mechanism 50 to axially retain the bone plate which may allow the surgeon to use the drill guide 10 as a plate holder. As the location post 152 is inserted into the slot end-hole 72 of the plate 70, the fingers 154 are forced together, causing them to exert an expansion spring force against the inner surface 172 of the slot end-hole 72, thereby locking the drill guide 10 to the plate 70. Although the expansion force may be sufficient to axially lock the drill guide to the plate, the location post remains rotatable within the hole 72, thus allowing the guide barrel 40 to be swiveled to align with a pair of bone screw holes 74R, L, as described with respect to the previous embodiment.

To increase the locking strength of the location post 152 within the slot end-hole 72 of the bone plate 70, the resilient fingers 154 may comprise one or more circumferential ridges 1154 which may engage the inner surface of the slot end-hole 72. This arrangement may be particularly effective where the slot end-hole 72 is threaded, because the circumferential ridges may engage a portion of the slot end-hole threads. Further, as illustrated in FIG. 18, the distal-most circumferential ridge 1155 of each resilient finger 154 may be configured to engage an underside surface 79 of the plate 70, thus providing an additional axial retention feature between the plate to the drill guide 10.

As shown in FIG. 11, drill bit 80 may comprise a proximal coupling end 802 and a distal drilling end 804. The proximal coupling end 802 may be configured to couple to an appropriate source of rotational motion, either hand or powered, and may assume any appropriate configuration known in the art. The distal drilling end 804 likewise may comprise drilling flutes 84 configured to drill into bone. Intermediate the proximal and distal ends 802, 804 the drill body 806 may comprise at least one shoulder region 810 configured to cooperate with an internal shoulder 150 of the drill guide barrel bore 48 to control the maximum distance which the drill is allowed to advance beyond the nose portion 42 of the guide barrel 40. This maximum distance may correspond to a maximum desired drilling depth, and may controlled by locating the cooperating shoulder regions 810, 150 of the drill 80 and guide barrel 40 appropriately.

Figure 12:
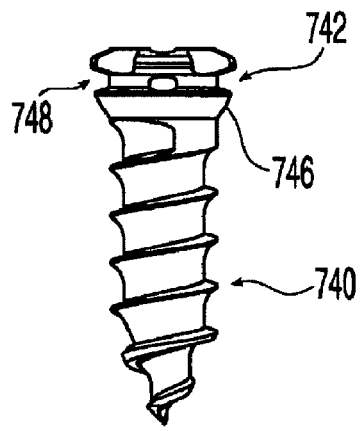
FIG. 12 is a side view of an exemplary bone screw for use with the bone fixation plate of FIG. 2A.
Figure 16:
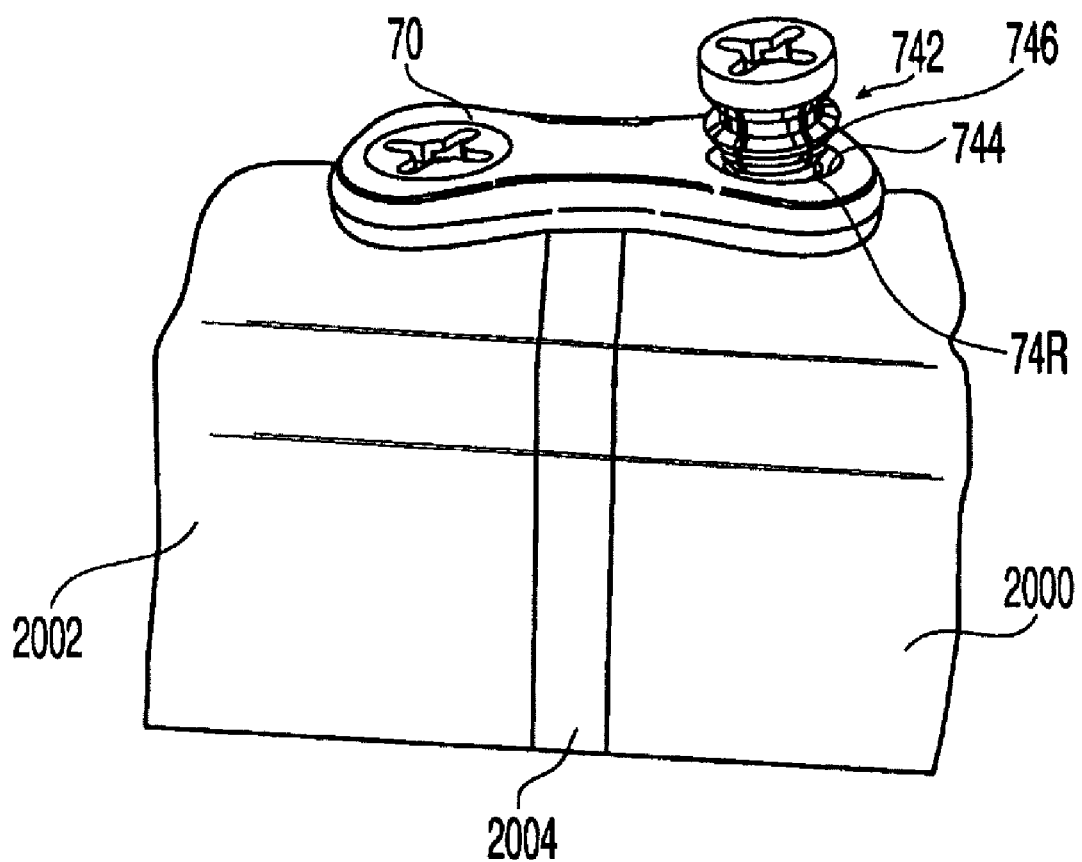
FIG. 16 is a perspective view of a bone plate fixed to adjacent vertebra using two pairs of bone screws, where the bone screws have been placed in holes drilled off-center of the fastener holes of the plate.

In an alternative embodiment, the drill guide barrel 40 and plate attachment mechanism 50 may be arranged so that the hole drilled in the bone may be slightly longitudinally offset from the center of the bone screw holes 74R, L located on one end of the bone plate 70. Drilling a hole in the bone which is offset from the bone screw hole 74R, L of the plate 70 may result in the head 742 of the bone screw 740 (FIG. 12) overhanging one side 744 (FIG. 13) of the screw hole 74R, L when the screw is initially inserted into the hole in the bone (FIG. 16). Thus, as the bone screw 740 is driven into the vertebra, the angled lower surface 746 of the screw head 742 may contact the side 744 of the screw hole, and as the bone screw 740 is driven further into the vertebra, the screw head may force the plate 70 to move longitudinally relative to the screw 740 until the screw is centered within the bone screw hole 74R, L. This arrangement may be used to move adjacent vertebra nearer to each other simply by tightening the bone screws that are drilled into the offset holes (i.e. compression of the intermediate disc space may be achieved). To effect such a compression, a first pair of bone screws may be inserted through a first pair of bone screw holes 74R, L and fully engaged with the underlying vertebra to lock the plate 70 to the first vertebra. Thereafter, the drill guide of the present embodiment may be used to prepare two bone screw holes that are longitudinally offset from the center of an adjacent pair of bone screw holes in the plate 70. A second set of bone screws then may be driven into the offset holes to achieve the above-described longitudinal movement between the plate and the screws. To achieve the desired offset, the distance between the guide barrel 40 and the guide barrel housing 156 may be varied as appropriate.

Figure 17:
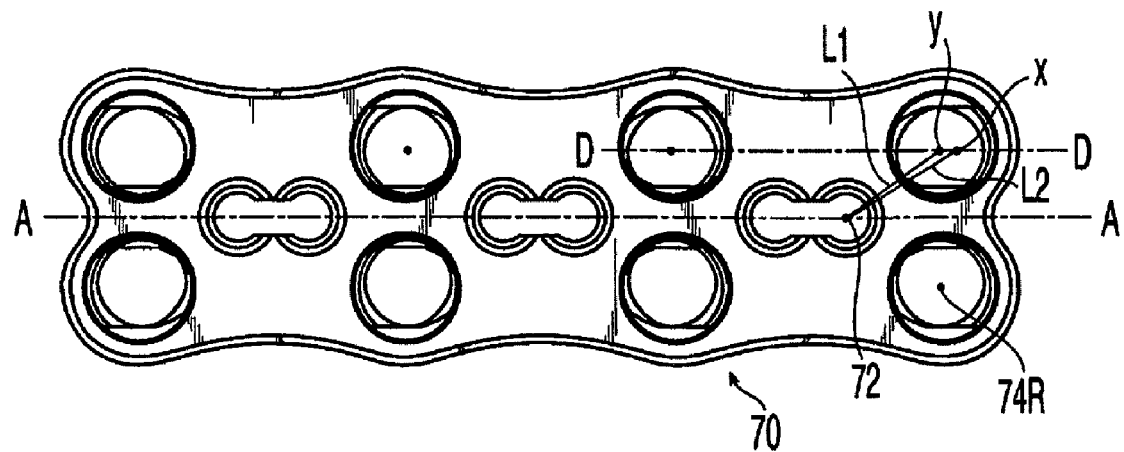
FIG. 17 is a top view of the bone plate of FIG. 2A, illustrating an offset bone screw hole.

As shown in FIG. 17, an exemplary offset bone hole insertion point is indicated as "X," while the center point of the bone screw hole 74R, L is indicated as "Y." The distance from the bone plate slot end-hole 72 to the center of the bone screw hole 74R, L is designated "L1," while the distance from the bone plate slot end-hole 72 to the center of the offset bone hole insertion point "X" is designated "L2." An axis "D-D" formed by points "X" and "Y" may be oriented substantially parallel to the longitudinal axis "A-A" of the bone plate 70. A bone screw 740 (FIG. 12) inserted into a hole formed at point "X" will, when tightened into the bone, move toward point "Y" due to the previously described interaction of the bone screw head 742 with the side 744 of the fastener hole 74R, L. This movement of the bone screw 740 along axis "D-D" will also move the attached bone segment 2002 along axis "D-D" toward the adjacent bone segment 2004, thus drawing the two bone segments closer together along axis "D-D."

In the embodiment illustrated in FIG. 16, the bone plate may be attached to adjacent vertebra 2002, 2004 of the spine such that the plate axis "A-A" may be substantially aligned with the longitudinal axis of the spine. Thus, compression of the disc space 2006 between the adjacent vertebra 2002, 2004, may be achieved substantially along the axis of the spine. Compression of the disc space in a direction substantially along the longitudinal axis of the spine may be important for a number of reasons, including the need to maintain the patient's anatomy in as normal a post-operative condition as possible. Additionally, where an Intervertebral spacer (e.g. a fusion spacer) has been installed between the vertebral end plates, compression along the spine axis serves to provide proper initial seating and loading of the spacer between the end plates.

To achieve this compression vector, the guide barrel 40 and location post 52 may be configured so that the center of the guide barrel 40 distal end 44 and center of the location post 52 may be separated by a distance equal to length "L2" so that when the drill guide barrel is rotated about the location post 52 it may be aligned with offset bone hole insertion point "X."

In one embodiment, the guide barrel 40 and barrel housing 156 may be configured so that the distance between points "X" and "Y" along axis "D-D" is about 0.5 mm, thus allowing approximately 0.5 mm of longitudinal compression of adjacent bone segments. In one embodiment, the drill guide barrel and housing may be configured so that the distance between points "X" and "Y" may be from about 0 mm to about 0.8 mm, thus allowing longitudinal compression of bone segments of from about 0 mm to about 0.8 mm when the fasteners are tightened within the appropriate bone screw holes.

While the bone plate, drill bit, and drill guide assembly are shown and described for use in fixing adjacent vertebra of the spine, it will be appreciated that the drill guide assembly may be utilized with any suitable bone plate or other structure that may be secured to bone using bone fasteners. Alternatively, the drill guide may be used without a bone plate to guide the drilling of fastener holes in bone at any appropriate location in the body.

The method of drilling holes in vertebrae with the system disclosed above will now be described. The surgeon may introduce a bone plate 70 through an incision in the patient's skin and move the plate to a desired location on the patient's spine. In an exemplary embodiment, the plate may have at least two pairs of bone screw holes 74R, L configured to engage two adjacent vertebra in the cervical region of the spine. After the plate has been appropriately placed on the spine, the drill guide 70 may be introduced through the incision and the location post 52 may be seated within a slot-end hole 72 associated with one of the two pairs of bone screw holes of the bone plate. The drill guide 10 may then be pivoted about the location post 52 to align the guide barrel with the first bone screw hole of the targeted pair of bone screw holes 74. Once the guide barrel 40 has been substantially aligned with a bone screw hole 74, downward pressure may be applied to the handle 20 to move the nose 42 of the guide barrel into engagement with the bone screw hole, thus precisely aligning the guide barrel with the screw hole 74. The surgeon may then sequentially insert, in any combination, an awl, tap and/or drill through the guide barrel bore to prepare a hole in the bone for receipt a bone screw. Preparing the hole in the bone using the drill guide 10 ensures that the hole is drilled in a vertebra at the proper angle coaxial with the fixation hole. After the first bone hole has been prepared, the drill guide may be rotated within the slot in the bone plate until the drill guide barrel is positioned above the second of the pair of bone screw holes. The process of applying pressure to engage the fixation hole and inserting the drill bit is then repeated. Holes coaxial with other pairs of fixation holes in the plate 70 may then be drilled by lifting the drill guide off the plate and seating the location post 52 in the slot-end hole 72 adjacent the next pair of targeted bone screw holes.

For embodiments of the drill guide 10 in which the location post 152 has an axial retention feature (e.g. resilient fingers) to retain the drill guide to the plate, the drill guide may be used to insert the plate through the incision in the patient and to align the plate at the desired location on the spine. Furthermore, once a pair of bone screw holes have been accessed and the appropriate holes drilled, a separating force must be applied between the drill guide of this embodiment and the plate to overcome the retaining force of the location post.

Additionally, when using the embodiment of the drill guide having a guide barrel without a conical nose portion, the step of pressing the guide barrel into the bone screw hole is omitted, and proper alignment of the drill guide barrel and the targeted screw hole may be achieved by simply pivoting the guide barrel into alignment over the screw hole. Alternatively, the user may employ the awl 90 (FIGS. 15A, B) to align the guide barrel 40 with the bone screw hole 74R, L. The awl 90 (FIGS. 15A, B) may be inserted through the guide barrel 40 so that the tapered nose portion 96 of the awl extends beyond the distal end 44 of the guide barrel and engages the tapered portion 174R, L of the targeted bone screw hole 74R, L. Once the awl tip 98 has been used to break the cortex of the underlying bone to form the initial entry hole, the drill 80 may thereafter be aligned within the initial entry hole, thus maintaining the proper drilling location. An exemplary awl may be that disclosed in co-pending United States non-provisional patent application entitled "Spring Loaded Awl," by Christopher J. Ryan, filed Aug. 19, 2003, the entire disclosure of which is expressly incorporated by reference herein.

Another embodiment of a drill guide 400 is shown in FIGS. 20A-21B. As seen in the perspective view of FIG. 20A, drill guide 400 may have an attachment portion 402 for engaging a handle (discussed in detail below), a shaft portion 404, and a engagement portion 406 for at least partially engaging a plate 450. Drill guide 400 may also have a bore 408 extending therethrough, which may be sized to receive a bone screw 410 therethrough, in addition to other objects and instruments, such as a drill bit, awl, tap, screwdriver, etc. Plate 450 may have a plurality of fixation holes 452, a plurality of drill guide keys 454, and a plurality of windows 456. Fixation holes 452 may receive a bone screw 410, which may be utilized to attach plate 450 to a bone or tissue. Drill guide keys 454 may assist in aligning and/or securing drill guide 400 relative to plate 450, as described in detail below. Windows 456 may assist a surgeon in visualizing a body site below plate 450, such as an intervertebral disc space.

Figure 20A:
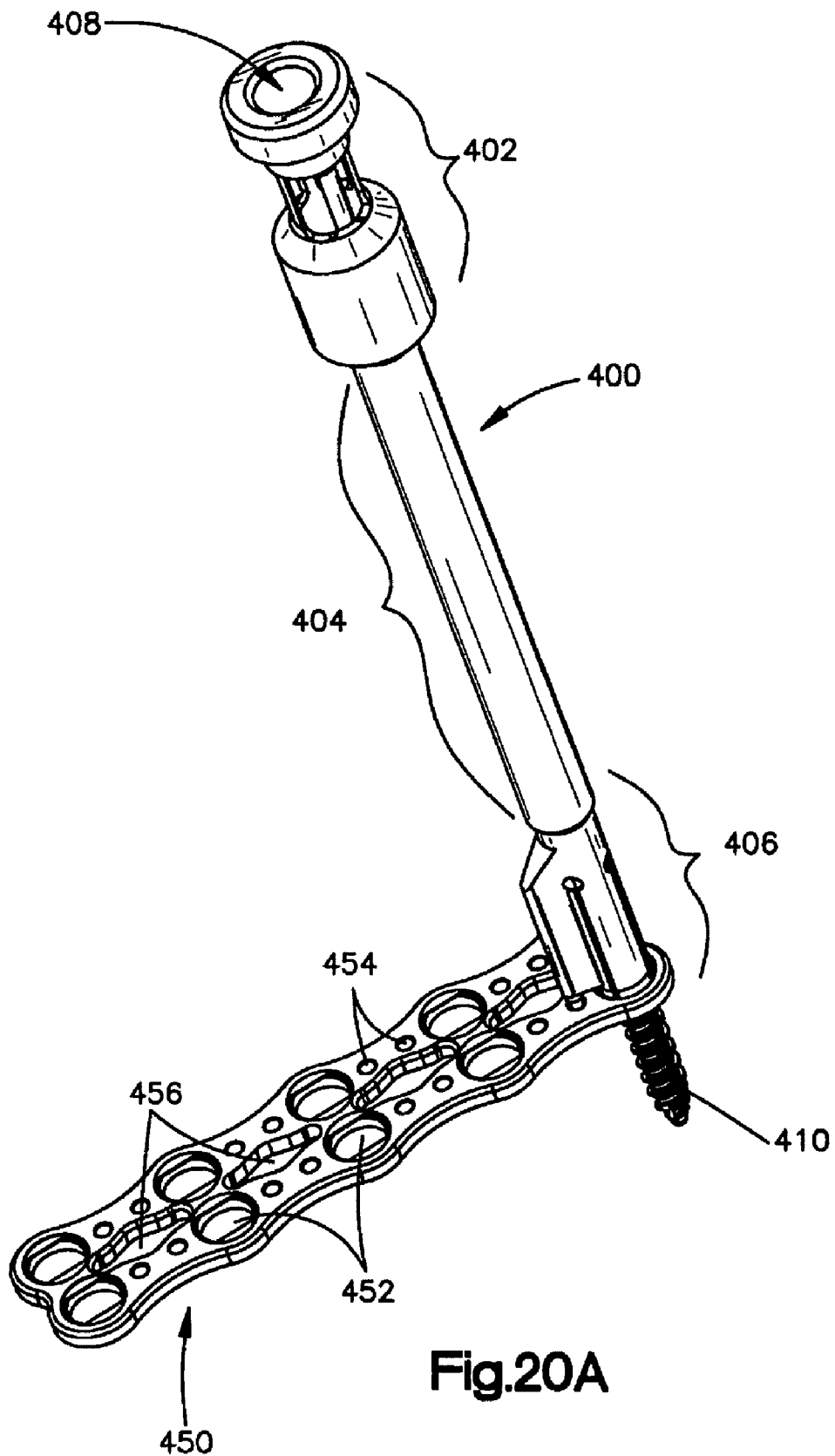
FIG. 20A is a perspective view of another embodiment of a drill guide engaging a plate.
Figure 20B:
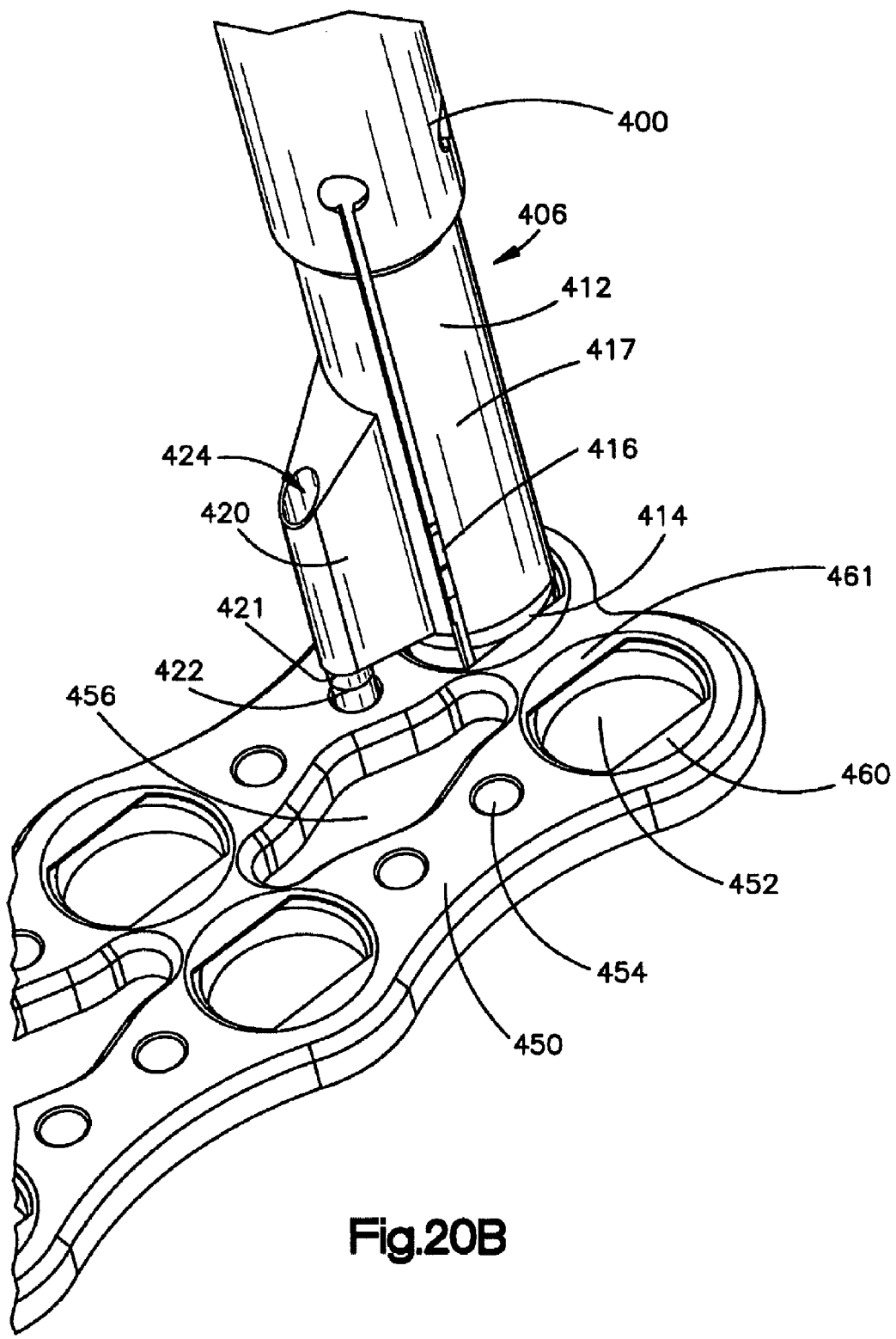
FIG. 20B is an enlarged view of the engagement of the drill guide of FIG. 20A with a plate.

FIG. 20B shows an enlarged view of the embodiment of FIG. 20A. As seen in this illustration, engagement portion 406 of drill guide 400 may have a barrel portion 412 and a pin portion 420. Barrel portion 412 may have tapered end portion 414, and may be at least partially inserted into a fixation hole 452, as described in detail below. Pin portion 420 may have a bore 424 therethrough, in which at least a portion of a position pin 422 may be received. Pin portion 420 may also have a leading surface 421. Shown in more detail in FIG. 20C, position pin 422 may engage a drill guide key 454 of plate 450. Concurrently to this engagement, tapered end portion 414 may be at least partially inserted into an adjacent fixation hole 452. Leading edge 415 (see FIG. 20C) of tapered end portion 414 may sit on the upper surface 461 of a clip 460 within fixation hole 452. Engagement portion 406 may have at least one channel 416 therein, which may create a plurality of resilient fingers 417 which may be expandable radially outward to enlarge bore 408 of drill guide 400 along engagement portion 406.

Figure 20C:
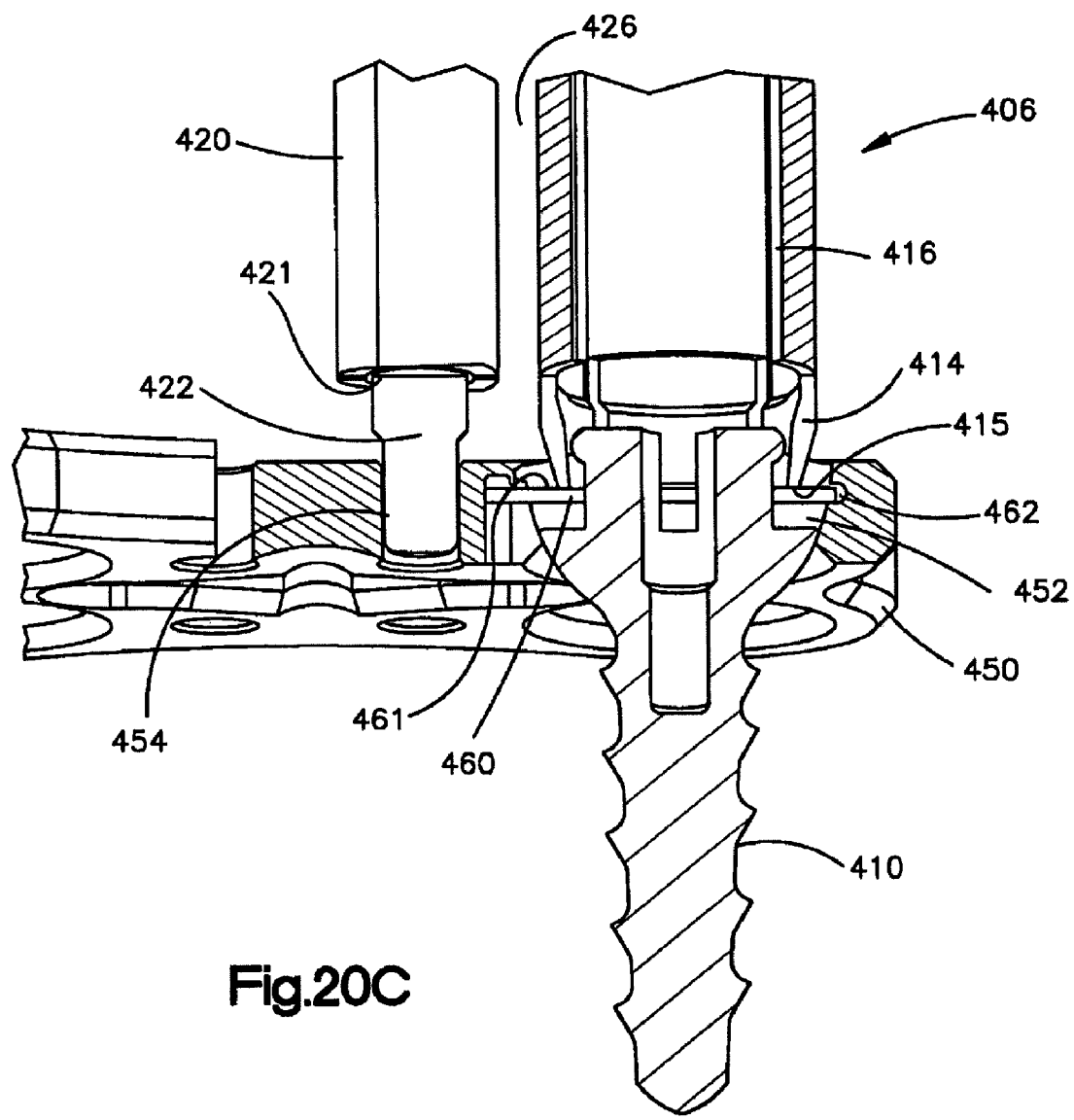
FIG. 20C is a partial cross-sectional view of the drill guide of FIG. 20B engaging a plate.

FIG. 20C shows a partial cross-sectional view of the embodiment of FIG. 20B with a bone screw 410 disposed within fixation hole 452 and in engagement with clip 460. As seen in this illustration, leading edge 415 of tapered end portion 414 rests on the upper surface 461 of clip 460, while position pin 422 partially extends into drill guide key 454. Thus, the engagement of position pin 422 to drill guide 454 may serve to provide a releasable, yet secure connection with plate 450 such that engagement portion 406 and bore 408 of drill guide 400 may be aligned with a fixation hole 452 for precise placement of bone screw 410 into fixation hole 452, or insertion of an instrument or object into bore 408 and through fixation hole 452. This arrangement may also be beneficial because drill guide 400 may not need to be removed from fixation hole 452 to insert a bone screw 410 into a fixation hole 452 after the drill guide 400 is used to guide a drill (not shown) through fixation hole 452 and into a bone surface below. As leading edge 415 of tapered end portion 414 is positioned on the top surface 461 of clip 460, instead of covering clip 460 or otherwise engaging clip 460, a bone screw 410 inserted via bore 408 to be inserted into fixation hole 452 may properly engage clip 460 without interference by drill guide 400. This may be beneficial, as a surgeon may therefore be able to engage drill guide 400 with a plate 450, perform any tapping, awling, drilling, or other procedure on a bone surface below plate 450 via a fixation hole 452, and thereafter insert a bone screw 410 (which may properly engage a clip 460) into the fixation hole 452 without having to remove or re-position drill guide 400 in any way. This advantage may make for more efficient and simpler surgical procedures, in addition to more consistent alignment of objects, instruments, and bone screws 410 via a single fixation hole 452.

Clip 460 may be disposed in a groove 462 within a plate, and preferably is comprised of a resilient expandable material that may partially expand and thereafter retract upon insertion of a larger object. There may also be a gap 426 between engagement portion 406 and pin portion 420 of drill guide 400.

FIGS. 21A-21B show further views of drill guide 400. As seen in the side view of FIG. 21A and the cross-sectional view of FIG. 21B, bore 408 may extend completely through attachment portion 402, shaft portion 404, and engagement portion 406 of drill guide 400. As also seen in FIG. 21B, pin portion 420 may have a partial bore 427 instead of a bore 424 completely therethrough (compare FIG. 20B). Partial bore 427 may have an opening 429 at leading surface 421, and may also have an end 428 disposed within pin portion 420. Both partial bore 427 and bore 424 may be selectively sized and shaped to receive a variety of position pins 422.

Figure 22:
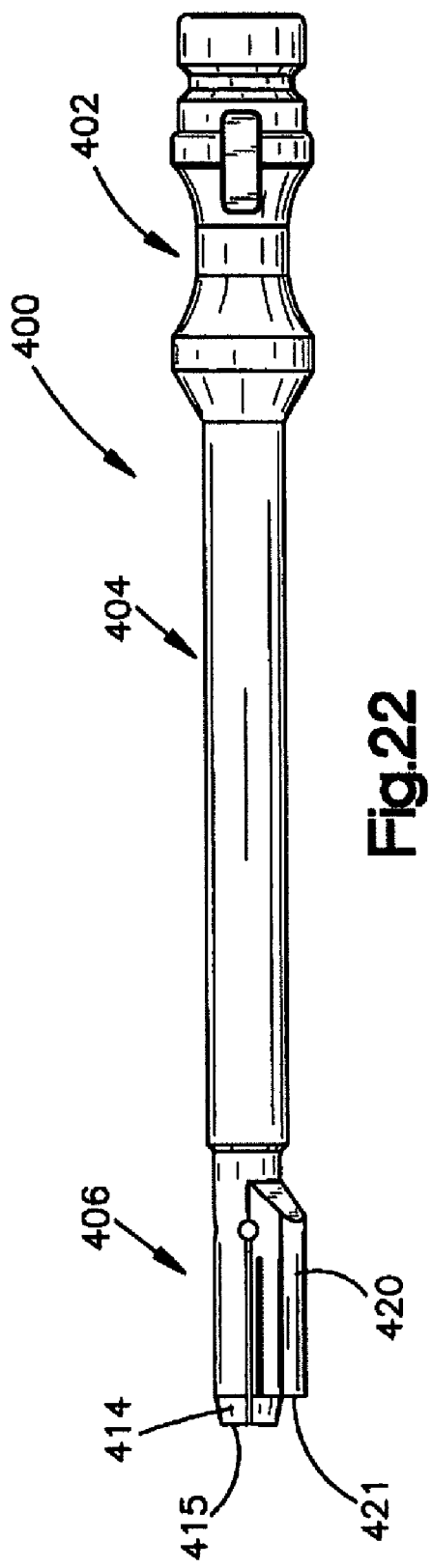
FIG. 22 is a side view of another embodiment of a drill guide.

FIG. 22 shows a side view of another embodiment of a drill guide 400. This embodiment has a different attachment portion 402, as compared to the embodiment shown in FIG. 21A. Handle portion 402 may be varied to accommodate and/or engage a variety of handles, as shown and described in more detail in relation to FIGS. 24A-26C.

Figure 23:
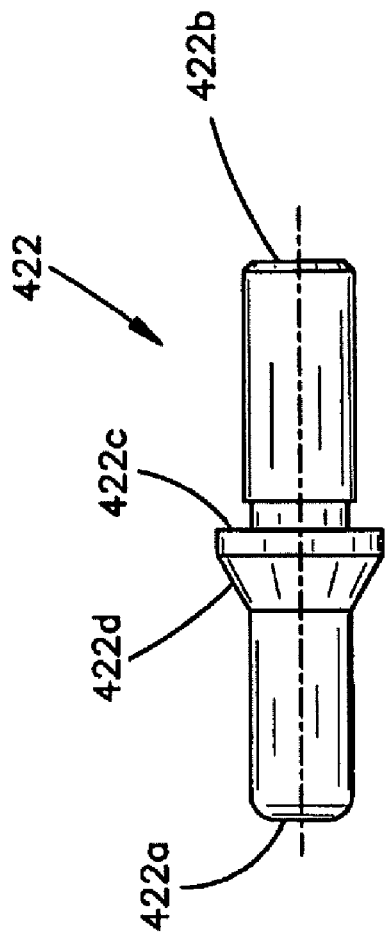
FIG. 23 is a side view of an embodiment of a position pin for use with the drill guide of FIGS. 20A-22.

FIG. 23 shows a side view of an embodiment of a position pin 422. Pin 422 may have a leading end 422a configured to engage a drill guide key 454, and a trailing end 422b configured to be inserted into a bore 424 or partial bore 427 of a pin portion 420. Pin 422 may also have an annular ledge 422c, which, when pin 422 is inserted into bore 424 or partial bore 427 of pin portion 420, may be situated adjacent to leading surface 421 of pin portion 420. Preferably the annular ledge 422c is sized larger than bore 424 or partial bore 427, so as to provide a stop that may limit the movement of pin 422 within a bore 424 or partial bore 427. Pin 422 may also have a tapered surface 422d, which may partially engage a drill guide key 454. Tapered surface 422d may be beneficial to create a frictional relationship between pin 422 and drill guide key 454, such that as the cross-sectional size of tapered portion 422d approximates the cross-sectional size of drill guide key 454, pin 422 is releasably, yet securely disposed with drill guide key 454. This embodiment of pin 422 is exemplary, as other sizes, shapes, dimensions, and characteristics are expressly contemplated, and will be appreciated by those skilled in the art.

Figure 24A:
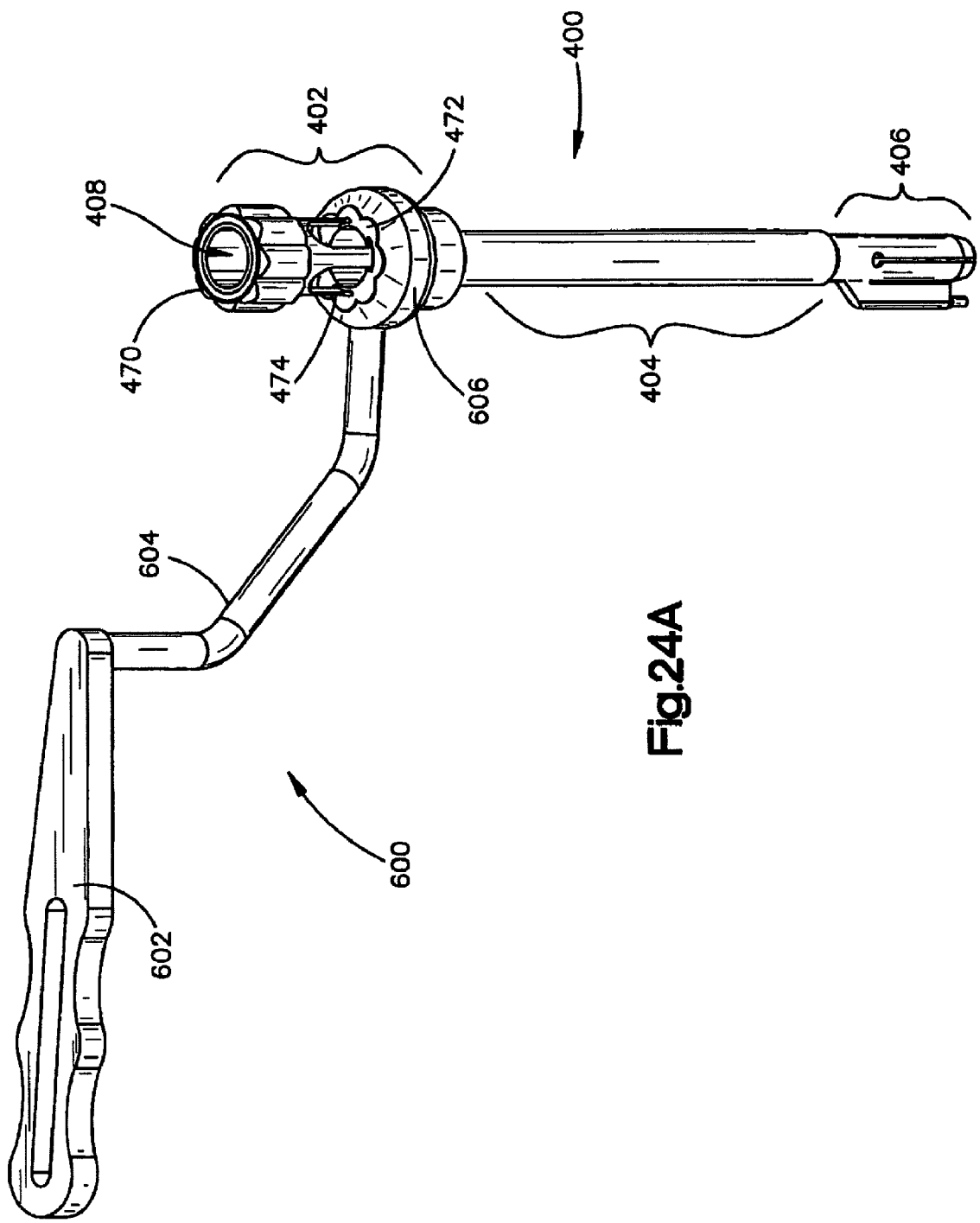
FIG. 24A is a perspective view of an embodiment of a drill guide with a handle.
Figure 24B:
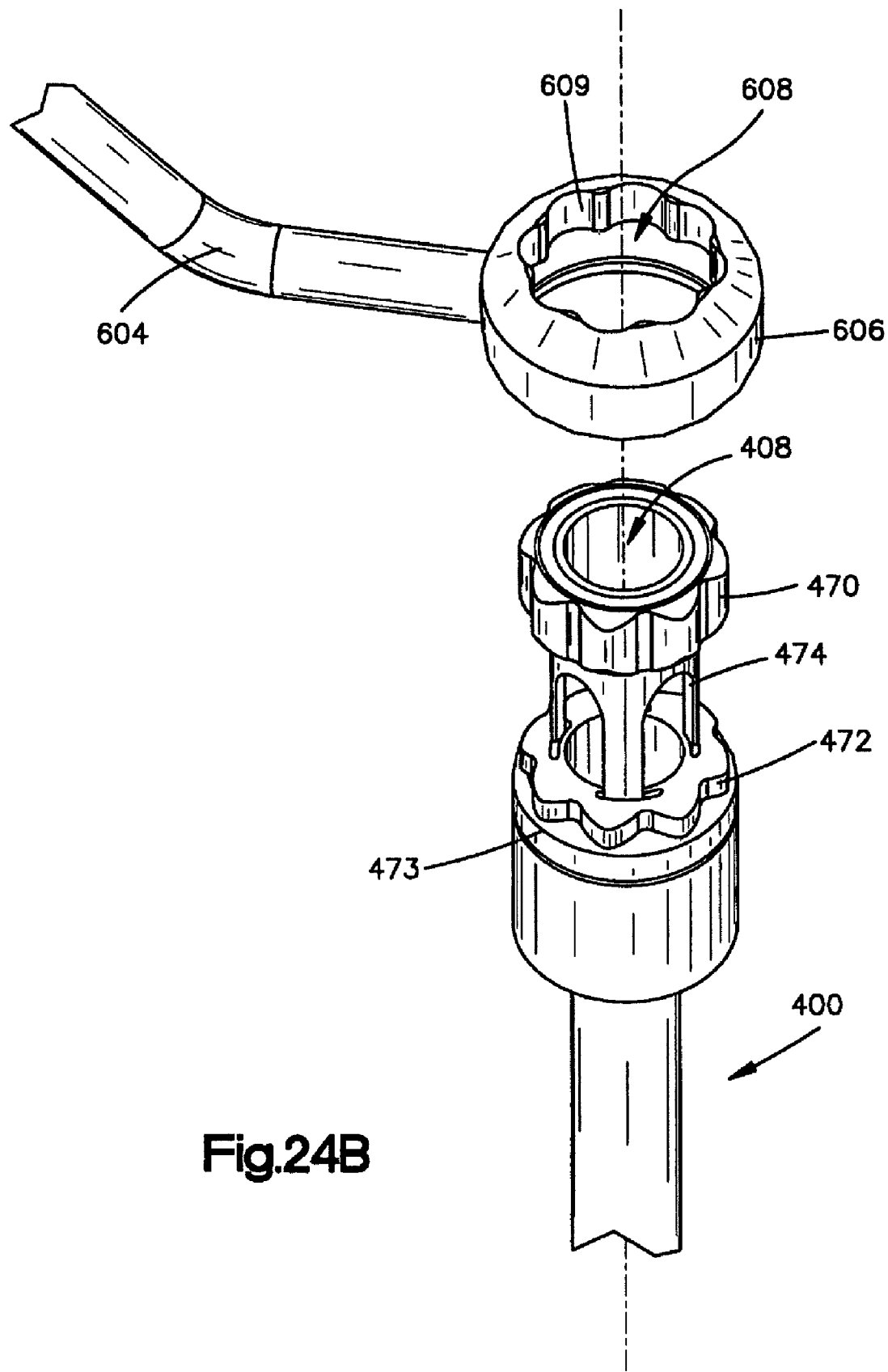
FIG. 24B is an enlarged view of the embodiment of FIG. 24A, wherein the handle is detached from the drill guide.

FIGS. 24A-24B show an embodiment of a drill guide 400 and handle 600. As seen in the perspective view of FIG. 24A, and enlarged view of FIG. 24B, handle 600 may have a gripping portion 602 and a connecting portion 604. Connecting portion 604 may have an annular ring 606 having a central opening 608 having a ridged inner surface 609. Attachment portion 402 of drill guide 400 may have an upper ridged portion 470 and a lower ridge portion 472, with an extension portion 474 extending therebetween. In use, annular ring 606 may be lowered onto attachment portion 402, to the extent that ridged inner surface 609 engages lower ridged portion 474, and rests against annular ledge 473, which preferably acts as a stop, as seen in FIG. 24A. Preferably, ridged inner surface 609 and lower ridged portion 474 may engage in a variety of rotational arrangements, such that handle 600 may assume a variety of angulations relative to drill guide 400.

Figure 25A:
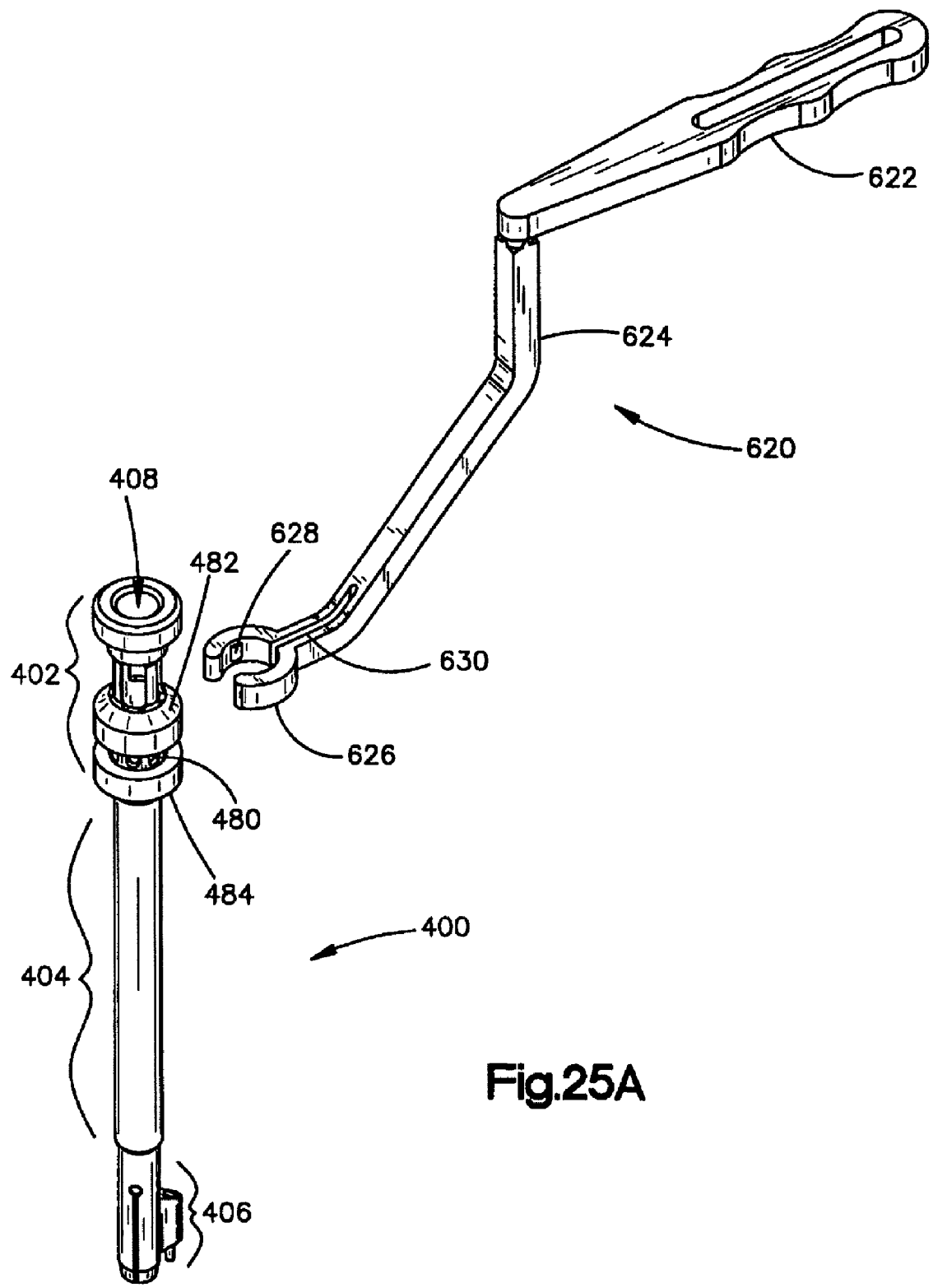
FIG. 25A is a perspective view of another embodiment of a drill guide with a handle, wherein the handle is detached from the drill guide.
Figure 25B:
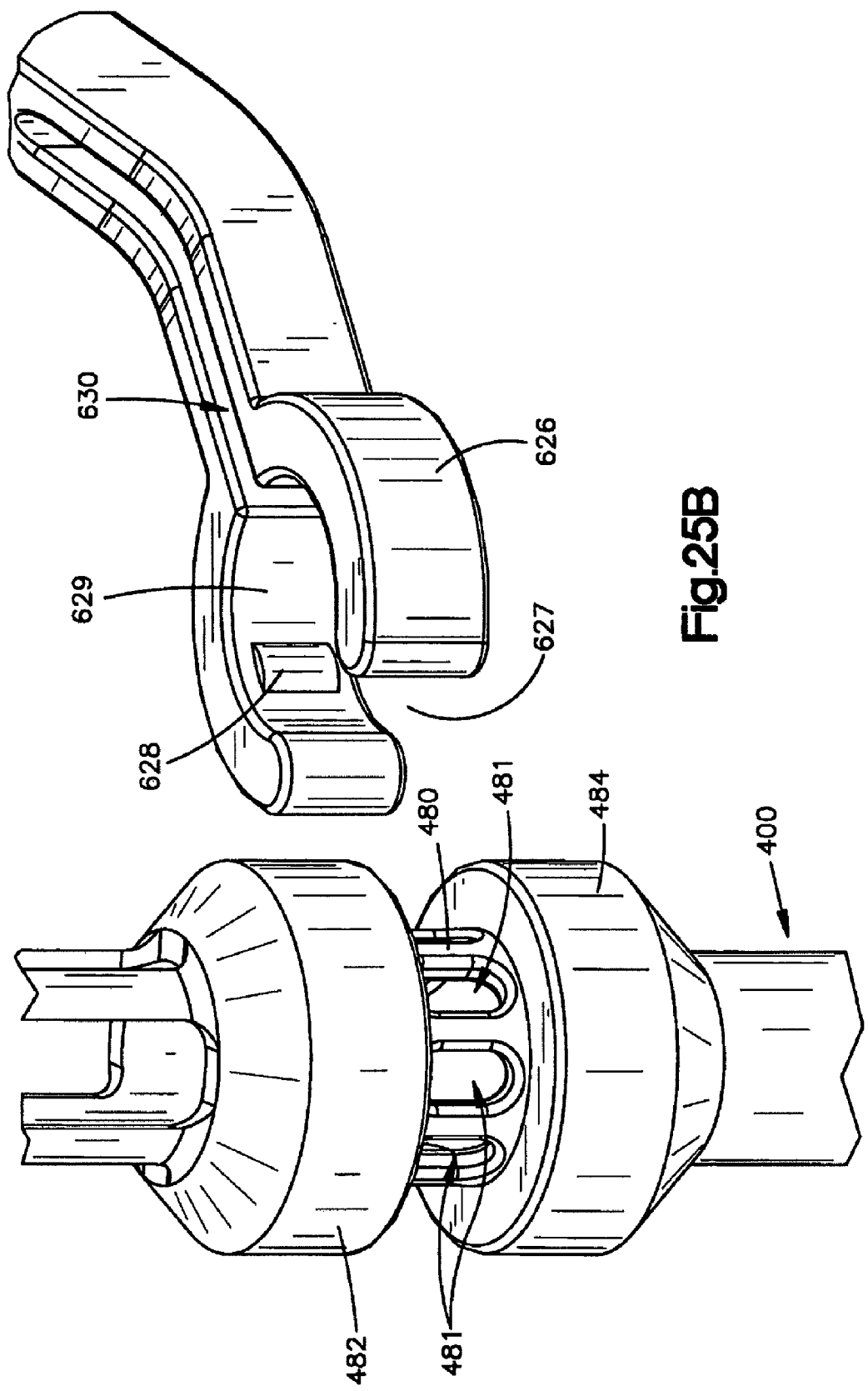
FIG. 25B is an enlarged view of the drill guide and handle of FIG. 25A.

FIGS. 25A-25B show another embodiment of a drill guide 400 and handle 620. As seen in the perspective view of FIG. 25A, and enlarged view of FIG. 25B, handle 620 may have a gripping portion 622 and a connecting portion 624. Connecting portion 624 may have a C-shaped portion 626 having an opening 627 and at least one projection 628 disposed on the inner surface 629 of C-shaped portion 626. Connecting portion 624 may also have a channel 630 extending from the inner surface 629 of the C-shaped portion 626, and toward gripping portion 622. Channel 630 may allow C-shaped portion 626 to expand outwards to engage a larger object therein. Attachment portion 402 of drill guide 400 in this embodiment may have upper and lower annular portions 482, 484, with an engagement portion 480 disposed therebetween. Engagement portion 480 may have a plurality of channels 481, wherein a channel 481 may be sized and configured to receive a projection 628 of connecting portion 624. In use, C-shaped portion 626 of handle 620 may engage attachment portion 402 by aligning the opening 627 with the engagement portion 480, and thereafter urging the C-shaped portion 626 toward the engagement portion 480, which may expand the C-shaped portion 626 outwards (which may be made possible by channel 630, described above). As each projection 628 becomes aligned with a channel 481, the C-shaped section 626 may snap back into its original form, thereby affixing the handle 620 to drill guide 400. Preferably, upper and lower annular portion 482, 484 are sized to prevent C-shaped portion 626 from sliding off of engagement portion 480. Again, it may be possible to engage C-shaped portion 626 with engagement portion 480 at a variety of rotational relationships, thereby providing a variety of possible angular arrangements between handle 620 and drill guide 400.

Figure 26A:
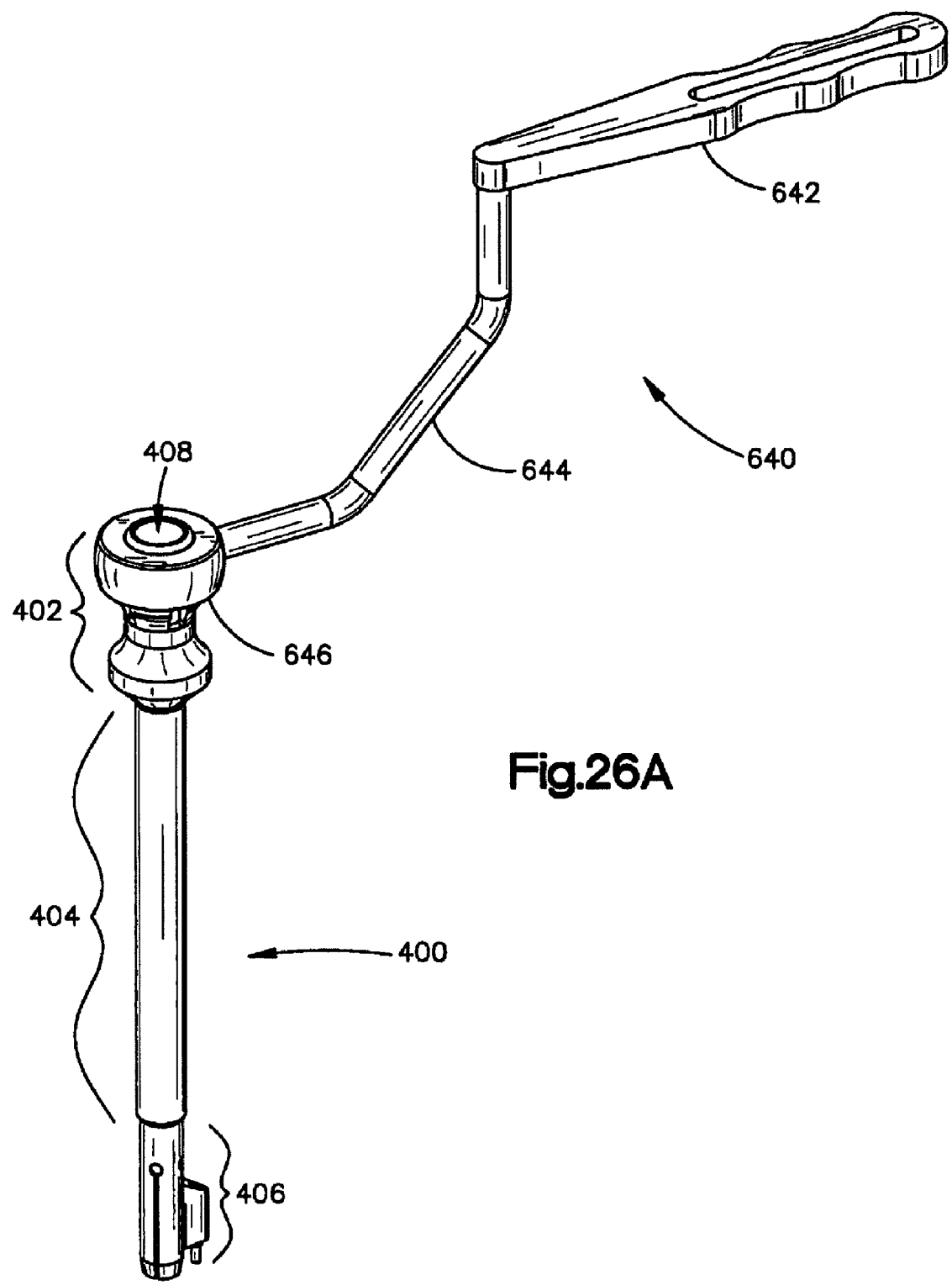
FIG. 26A is a perspective view of yet another embodiment of a drill guide with a handle.

FIGS. 26A-26C show yet another embodiment of a drill guide 400 and handle 640. As seen in the perspective view of FIG. 26A, the enlarged view of FIG. 26B, and the transparent view of FIG. 26C, handle 640 may have a gripping portion 642 and a connecting portion 644. Connecting portion 644 may have an annular ring 646 with a central opening 648 having an inner surface 649. A spring 650 may be disposed along the inner surface 649, and may have a substantially circular shape. Spring 650 preferably is flexible. Attachment portion 402 of drill guide 400 may have a upper and lower annular portion 492, 494 with a recessed annular portion 490 therebetween. In use, the annular ring 646 of connecting portion 644 may be lowered onto attachment portion 402, such that spring 650 expands when passed over upper annular portion 492, and contracts when aligned with recessed annular portion 490. Accordingly, it is preferable that lower annular portion 494 be sized larger than the recessed annular portion 490. Moreover, it may be preferable to position annular ring 646 such that the lower surface 647 of annular ring 646 rests on annular ledge 496 of attachment portion 402, thereby preventing annular ring 646 from traveling farther down attachment portion 402. As with previous embodiments of handles 600, 620 described above, handle 640 may assume a variety of angular arrangements relative to drill guide 400, as annular ring 646 may fit onto attachment portion 402 in a variety of rotational positions.

While the embodiments shown herein generally utilize a clip for engaging a bone screw, it is expressly contemplated that other suitable retention mechanisms may be employed, as will be appreciated by those of skill in the art.

While the invention has been shown and described herein with reference to particular embodiments, it is to be understood that the various additions, substitutions, or modifications of form, structure, arrangement, proportions, materials, and components and otherwise, used in the practice and which are particularly adapted to specific environments and operative requirements, may be made to the described embodiments without departing from the spirit and scope of the present invention. For example, various means may be used to attach the plate holder to the bone plate or to the drill guide assembly. In addition, the plate may be of various thicknesses, shapes, and contours; and have various fixation hole configurations. Accordingly, it should be understood that the embodiments disclosed herein are merely illustrative of the principles of the invention. Various other modifications may be made by those skilled in the art which will embody the principles of the invention and fall within the spirit and the scope thereof.

What is claimed is:

1. A method of inserting a bone screw comprising the steps of:
   (a) providing a drill guide including a shaft having a front end, a rear end, and a bore therethrough, and a housing having a proximal end, a distal end and an alignment portion, the proximal end being coupled to the shaft, the housing further including a slot extending from the distal end of the housing to form a gap between the distal end of the housing and the distal end of the shaft, the slot terminating in an enlarged opening, and providing a bone plate having a first fixation hole for receiving a bone screw, a first drill guide key and a first retention mechanism for engaging a first bone screw;
   (b) associating the drill guide with the plate at a desired angle including:
      fixedly engaging the first guide key with the alignment portion; and
      inserting an outer diameter of the front end of the shaft within a diameter of the first fixation hole, wherein the first fixation hole diameter is larger than the outer diameter, and aligning the bore with the first fixation hole without fixedly associating the front end with the plate; and
      contacting the front end of the shaft with a top surface of the first retention mechanism;
   (c) inserting an instrument into the bore;
   (d) removing the instrument from the bore;
   (e) inserting a bone screw into the bore; and
   (f) engaging the first bone screw with the first retention mechanism without substantially displacing the drill guide relative to the bone plate.

2. The method of claim 1, wherein the alignment portion is offset from the front end.

3. The method of claim 2, wherein the alignment portion is configured to engage the bone plate proximate the first fixation hole.

4. The method of claim 1, wherein the front end is not fixedly attached to the bone plate in steps (b)-(f).

5. The method of claim 1, wherein step (c) further comprises drilling a bore into a bone surface suitable for receiving at least a portion of the bone screw.

6. The method of claim 1, wherein the drill guide further comprises a handle, and wherein step (b) further comprises manipulating the handle to achieve the desired angle.

7. The method of claim 1, further comprising the steps of disengaging the drill guide from the bone plate, associating the drill guide with the bone plate at a different location and inserting a second bone screw into a second fixation hole.

* * * * *